United States Patent [19]
Floyd et al.

[11] Patent Number: 4,748,239
[45] Date of Patent: May 31, 1988

[54] BENZAZEPINE DERIVATIVES

[75] Inventors: David Floyd, Pennington; John Krapcho, Somerset, both of N.J.

[73] Assignee: E. R. Squibb & Sons, Inc., Princeton, N.J.

[21] Appl. No.: 42,187

[22] Filed: Apr. 24, 1987

Related U.S. Application Data

[63] Continuation-in-part of Ser. No. 935,995, Nov. 28, 1986, abandoned, which is a continuation-in-part of Ser. No. 800,936, Nov. 22, 1985, abandoned, which is a continuation-in-part of Ser. No. 743,841, Jun. 12, 1985, abandoned.

[51] Int. Cl.$^4$ .................... C07D 223/16; A61K 31/55
[52] U.S. Cl. .................................................... 540/523
[58] Field of Search ........................................ 540/523

[56] References Cited

U.S. PATENT DOCUMENTS

| 3,312,691 | 4/1967 | Werner | 540/523 |
| 3,330,823 | 7/1967 | Bernstein et al. | 540/523 |
| 3,562,257 | 2/1971 | Kugita et al. | 540/491 |
| 3,748,321 | 7/1973 | Krapcho | 540/523 |

FOREIGN PATENT DOCUMENTS 0205334 12/1986 European Pat. Off. ............ 540/523

OTHER PUBLICATIONS

Yabana et al., J. Cardiovascular Pharm., vol. 7, p. 152, (1985).
Schoemaker et al., J. Cardiovascular Pharm., vol. 9, p. 173, (1987).
Chem. Pharm. Bull., vol. 33, pp. 634–641, (1985).
Goodman and Gilman's, "The Pharmacological Basis of Therapeutics", Seventh Edition, (MacMillan), (1985), pp. 816–819.

Primary Examiner—Robert T. Bond
Attorney, Agent, or Firm—Lawrence S. Levinson; Donald J. Barrack

[57] ABSTRACT

Vasodilating activity is exhibited by compounds having the formula

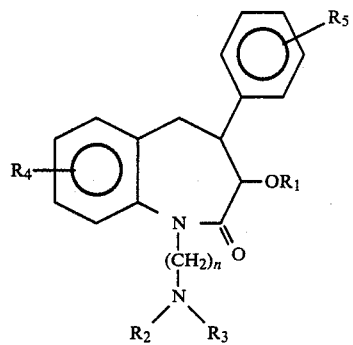

and pharmaceutically acceptable salts thereof.

30 Claims, No Drawings

BENZAZEPINE DERIVATIVES

This application is a continuation-in-part of U.S. patent application Ser. No. 935,995, filed Nov. 28, 1986, and now abandoned, which is a continuation-in-part of U.S. patent application Ser. No. 800,936, filed Nov. 22, 1985, and now abandoned, which is a continuation-in-part of U.S. patent application Ser. No. 743,841, filed June 12, 1985, and now abandoned.

BRIEF DESCRIPTION OF THE INVENTION

Compounds having the formula

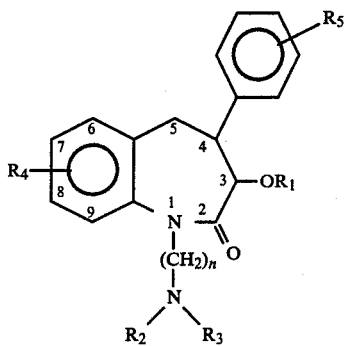

I and the pharmaceutically acceptable salts thereof, have useful vasodilating activity. In formula I, and throughout the specification, the symbols are as defined below.

$R_1$ is hydrogen, alkyl, alkanoyl, alkenyl, arylcarbonyl, heteroarylcarbonyl or

$R_2$ and $R_3$ are each independently hydrogen, alkyl, cycloalkyl or arylalkyl, or $R_2$ and $R_3$ together with the nitrogen atom to which they are attached are pyrrolidinyl, piperidinyl, or morpholinyl;

$R_4$ and $R_5$ are each independently hydrogen, halogen, alkyl, alkoxy, aryloxy, arylalkoxy, diarylalkoxy, arylalkyl, cyano, hydroxy, alkanoyloxy,

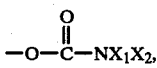

fluoro substituted alkoxy, fluoro substituted alkyl, (cycloalkyl)alkoxy, —$NO_2$, —$NX_3X_4$, —$S(O)_m$alkyl, —$S(O)_m$aryl,

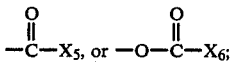

n is 2 or 3;

m is 0, 1 or 2;

$X_1$ and $X_2$ are each independently hydrogen, alkyl, aryl or heteroaryl, or $X_1$ and $X_2$ together with the nitrogen atom to which they are attached are pyrrolidinyl, piperidinyl or morpholinyl;

$X_3$ and $X_4$ are each independently hydrogen, alkyl, alkanoyl, arylcarbonyl, heteroarylcarbonyl, or

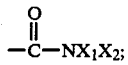

$X_5$ is hydroxy, alkoxy, aryloxy, amino, alkylamino or dialkylamino; and $X_6$ is alkyl, alkoxy or aryloxy; with the proviso that if $R_4$ is a 7-alkyl group, it must have a tertiary carbon atom bonded to the ring.

Listed below are definitions of various terms used to describe the benzazepines of this invention. These definitions apply to the terms as they are used throughout the specification (unless they are otherwise limited in specific instances) either individually or as part of a larger group.

The terms "alkyl" and "alkoxy" refer to both straight and branched chain groups. Those groups having 1 to 10 carbon atoms are preferred.

The term "alkenyl" refers to both straight and branched chain groups. Those groups having 2 to 10 carbon atoms are preferred.

The term "aryl" refers to phenyl and substituted phenyl. Exemplary substituted phenyl groups are phenyl groups substituted with 1, 2 or 3 amino (—$NH_2$), alkylamino, dialkylamino, nitro, halogen, hydroxyl, trifluoromethyl, alkyl (of 1 to 4 carbon atoms), alkoxy (of 1 to 4 carbon atoms), alkanoyloxy, carbamoyl, or carboxyl groups.

The term "alkanoyl" refers to groups having the formula

Those alkanoyl groups having 2 to 11 carbon atoms are preferred.

The term "heteroaryl" refers to an aromatic heterocyclic group having at least one heteroatom in the ring. Preferred groups are pyridinyl, pyrrolyl, imidazolyl, furyl, thienyl, or thiazolyl.

The term "cycloalkyl" refers to groups having 3, 4, 5, 6 or 7 carbon atoms.

The term "halogen" refers to fluorine, chlorine, bromine and iodine.

The terms "fluoro substituted alkyl" and "fluoro substituted alkoxy" refer to alkyl and alkoxy groups (as described above) in which one or more hydrogens have been replaced by fluorine atoms. Exemplary groups are trifluoromethyl, 2,2,2-trifluoroethyl, pentafluoroethyl, fluoromethoxy, difluoromethoxy, etc.

The compounds of formula I form acid-addition salts with inorganic and organic acids. These acid-addition salts frequently provide useful means for isolating the products from reaction mixtures by forming the salt in a medium in which it is insoluble. The free base may then be obtained by neutralization, e.g., with a base such as sodium hydroxide. Any other salt may then be formed from the free base and the appropriate inorganic or organic acid. Illustrative are the hydrohalides, especially the hydrochloride and hydrobromide, sulfate, nitrate, phosphate, borate, acetate, tartrate, maleate, citrate, succinate, benzoate, ascorbate, salicylate, methanesulfonate, benzenesulfonate, toluenesulfonate and the like.

The carbon atoms in the 3 and 4-positions of the benzazepine nucleus of the compound of formula I are asymmetric carbons. The compounds of formula I, therefore, exist in enantiomeric and diastereomeric forms and as racemic mixtures thereof. All are within the scope of this invention. It is believed that those compounds of formula I which have the d-cis configuration are the most potent and are therefore preferred.

DETAILED DESCRIPTION OF THE INVENTION

The compounds of formula I and the pharmaceutically acceptable salts thereof are useful as cardiovascular agents. These compounds act as vasodilators and are especially useful as anti-hypertensive agents. By the administration of a composition containing one (or a combination) of the compounds of this invention the blood pressure of a hypertensive mammalian (e.g., human) host is reduced. Daily doses of about 0.1 to 100 mg. per kilogram of body weight per day, preferably about 1 to about 50 mg. per kilogram per day, are appropriate to reduce blood pressure, and can be administered in single or divided doses. The substance is preferably administered orally, but parenteral routes such as the subcutaneous, intramuscular, or intravenous routes can also be employed.

As a result of the vasodilating activity of the compounds of formula I, it is believed that such compounds in addition to being anti-hypertensives may also be useful as anti-arrhythmic agents, as anti-anginal agents, as anti-fibrillatory agents, as anti-asthmatic agents, and in limiting myocardial infarction.

The compounds of this invention can also be formulated in combination with a diuretic or an angiotensin converting enzyme inhibitor. Suitable diuretics include the thiazide diuretics such as hydrochlorothiazide and bendroflumethiazide and suitable angiotensin converting enzyme inhibitors include captopril.

The compounds of formula I can be prepared by first reacting a 2-nitrotoluene having the formula

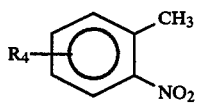

with a benzylidine malonate having the formula

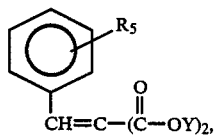

wherein Y is alkyl. The reaction can be run in a polar nonprotic solvent (e.g., dimethylformamide), in the presence of a strong base such as sodium hydride, and yields a product having the formula

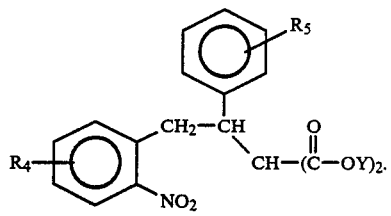

Reduction of a compound of formula IV yields the corresponding compound having the formula

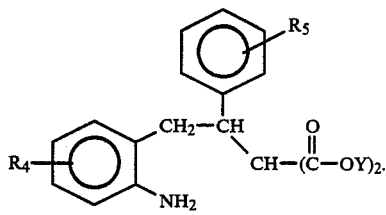

The reduction can be accomplished by catalytic hydrogenation (using, for example, palladium on charcoal as a catalyst) or using a chemical reducing agent (e.g., ferrous sulfate or stannous chloride).

Treatment of an amine of formula V with an alkali metal alkoxide (e.g., sodium methoxide) and an alcohol (e.g., methanol) yields the corresponding benzazepine having the formula

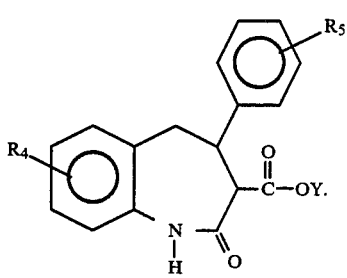

Reaction of a compound of formula VI with a strong base (e.g., lithium diisopropylamide, potassium hexamethyldisilazide, or potassium t-amylate) in an etheral solvent, such as tetrahydrofuran, or a polar nonprotic solvent, e.g., dimethylformamide, at low temperature in the presence of anhydrous oxygen gas yields the corresponding compound having the formula

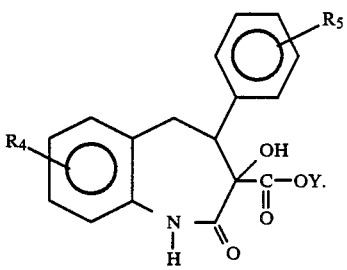

Alternatively, a compound of formula VII can be prepared by first cooling a compound of formula VI to a greatly reduced temperature (e.g., about −78° C.) in a solvent such as tetrahydrofuran and treating it with a strong base (e.g., lithium diisopropylamide or potassium hexamethyldisilazide). Treatment of the compound with anhydrous oxygen gas in the presence of triethyl phosphite yields the desired compound of formula VII.

Decarboxylation of a compound of formula VII can be accomplished by treating the compound with excess lithium iodide in hot pyridine to obtain a mixture of isomers having the formulas

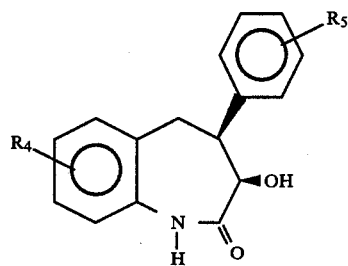

VIIIa cis isomer and

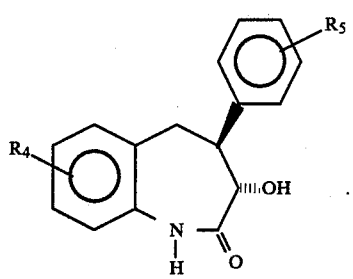

VIIIb trans isomer

The preferred cis isomer is generally the predominant isomer formed during the above reaction. The isomers can be separated using art recognized techniques such as crystallization or chromatography. Alternatively, the reactions described hereinafter can be run using the diastereomeric mixture (mixture of compounds of formulas VIIIa and VIIIb). The isomeric mixture can be separated into its component isomers at any point during the reaction sequence.

Treatment of a compound of formula VIIIa or VIIIb with an alkali metal hydride (e.g., sodium hydride) in an inert solvent such as dimethylformamide or dimethylsulfoxide, followed by reaction with a compound having the formula halogen-$(CH_2)_n$—$NR_2R_3$,       IX yields the corresponding compound having the formula

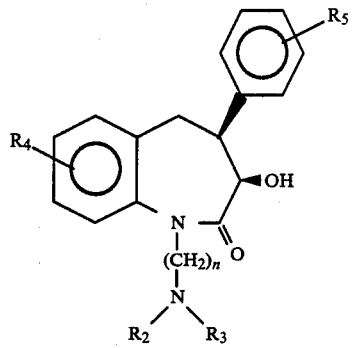

X or corresponding trans isomer; i.e., a product of formula I wherein $R_1$ is hydrogen.

Alternatively, compounds of formula X can be prepared by reacting a compound of formula VIII with a compound of formula IX under phase transfer conditions in a mixture of water and dichloromethane or toluene with an appropriate base (e.g., barium hydroxide) and catalyst (e.g., benzyl trimethylammonium chloride).

The compounds of formula X (or corresponding trans isomer) can be acylated or alkylated using conventional techniques to obtain those products of formula I wherein $R_1$ is other than hydrogen. For example, a compound of formula X (or corresponding trans isomer) can be reacted with a halide of the formula $R_1$-halogen       XI in the presence of a base. Alternatively, the acylation can be accomplished using an acid anhydride.

The resolved enantiomers of the compounds of this invention can be prepared by first hydrolyzing a compound of formula VI to obtain the corresponding carboxylic acid having the formula

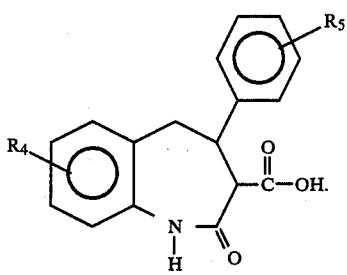

XII

The hydrolysis can be accomplished, for example, by treating a compound of formula VI with an alkali metal hydroxide in an alcohol (e.g., potassium hydroxide in methanol).

A carboxylic acid of formula XII can be resolved using a chiral amine. Reaction of the acid and amine in an appropriate solvent yields the diastereomeric salts which can be separated using conventional techniques such as crystallization. Regeneration of the carboxylic acid from the pure diastereomeric salt followed by esterification yields the desired nonracemic form of a compound of formula VI. Alternatively, compounds of formula VI can be generated directly from the diastereomeric salts by treatment with an alkyl halide in dimethylformamide in the presence of an inorganic base (e.g., potassium bicarbonate). This nonracemic compound can be converted to the corresponding nonracemic product of formula I via the nonracemic form of intermediates of formulas VII and VIII using the procedures described above.

Alternatively, the resolved enantiomers of the compounds of this invention can be prepared by the reaction of a compound of formula X with a chiral carboxylic acid in an appropriate solvent. The resulting diastereomeric salts can be separated by recrystallization.

In the reactions described above for preparing the compounds of this invention, it may be necessary to protect reactive substituents (e.g., hydroxy and amino) from involvement in the reactions. Protection of the substituents, and the necessary deprotection, can be accomplished using standard techniques. This is further illustrated in the examples showing the preparation of products of formula I wherein $R_2$ and/or $R_3$ are hydrogen.

Preferred members of each of the substituent groups of the benzazepines of formula I are as follows: $R_1$ is acetyl; n is 2; $R_2$ and $R_3$ are each methyl or $R_2$ is hydrogen and $R_3$ is methyl; $R_4$ is trifluoromethyl (especially 7-trifluoromethyl and 6-trifluoromethyl); and $R_5$ is 4-methoxy.

The following examples are specific embodiments of this invention.

EXAMPLE 1

(cis)-3-(Acetyloxy)-7-chloro-1-[2-(dimethylamino)ethyl]-1,3,4,5-tetrahydro-4-(4-methoxyphenyl)-2H-1-benzazepin-2-one, monohydrochloride

METHOD I (A)

[2-(5-Chloro-2-nitrophenyl)-1-(4-methoxyphenyl)ethyl]propanedioic acid, dimethyl ester To a stirred mixture of dimethyl p-methoxybenzylidene malonate (40 g, 0.16 mole) and 60% dispersion of sodium hydride (9.6 g, 0.24 mole) in 350 ml of dry dimethylformamide, was added dropwise over 2 hours a solution of 5-chloro-2-nitrotoluene (30 g, 0.176 mole) in 30 ml of dimethylformamide. The reaction was stirred at room temperature for 6 hours, then quenched with glacial acetic acid (15.4 ml, 0.26 mole). The solvent was removed in vacuo and the residue was triturated with water. The yellow solids were filtered and triturated with methanol to yield 50.3 g of a white solid, melting point 128.5°–130.5° C.

(B)

[2-(2-Amino-5-chlorophenyl)-1-(4-methoxyphenyl)ethyl-propanedioic acid, dimethyl ester To a refluxing mixture of [2-(5-chloro-2-nitrophenyl)-1-(4-methoxyphenyl)ethyl]propanedioic acid, dimethyl ester (40 g, 95.0 mmole) and hydrated ferrous sulfate (184.5 g, 0.663 mole) in a (1:10 solution of methanol:water (1.2 L) was added concentrated ammonium hydroxide (142.5 ml) over a 30 minute period. The reaction was stirred at reflux for 20 minutes then cooled to room temperature. Ethyl acetate and Celite were added and the mixture was filtered through Celite. The filtrate was partitioned between ethyl acetate and water. The organic phase was dried over magnesium sulfate and concentrated in vacuo. The product was recrystallized from isopropyl alcohol to yield 28.22 g of the title compound, melting point 114°–116° C.

(C)

7-Chloro-1,3,4,5-tetrahydro-3-(methoxycarbonyl)-4-(4-methoxyphenyl)-2H-1-benzazepin-2-one To a solution of [2-(2-amino-5-chlorophenyl)-1-(4-methoxyphenyl)ethyl]propanedioic acid, dimethyl ester (23.2 g, 59.2 mmole) in methanol (200 ml) was added a 25% solution of sodium methoxide in methanol (16 ml, 69.97 mmole). The solution was refluxed for 3 hours under argon. The reaction was cooled to room temperature and treated with 200 ml 1N hydrochloric acid. A white precipitate was filtered and washed with water, methanol, and dried in vacuo to yield 19.5 g of the title compound, melting point 189°–190.5° C.

(D)

7-Chloro-1,3,4,5-tetrahydro-3-hydroxy-3-(methoxycarbonyl)-4-(4-methoxyphenyl)-2$\underline{H}$1-benzazepin-2-one Oxygen was bubbled through a solution of 7-chloro-1,3,4,5-tetrahydro-3-(methoxycarbonyl)-4-(4-methoxyphenyl)-2H-1-benzazepin-2-one (7.0 g, 19.46 mmole) in 100 ml of dry tetrahydrofuran at 0° C. while a 0.67M solution of potassium hexamethyldisilazide in toluene (87.64 ml, 58.76 mmole) was added dropwise over 15 minutes. The reaction was continued for 1 hour with the continued bubbling of oxygen at 0° C. The reaction was quenched with 75 ml of a 5% solution of potassium bisulfate, followed by the addition of solid sodium sulfite and 10 ml of methanol. The reaction was stirred for 30 minutes and extracted twice with ethyl acetate. The combined organic layers were washed with 1N hydrochloric acid, saturated sodium bicarbonate, and dried over magnesium sulfate. The solvent was removed in vacuo and the residue was recrystallized from isopropyl alcohol to yield 4.5 g of the title compound.

(E)

(cis)-7-Chloro-1,3,4,5-tetrahydro-3-hydroxy-4-(4-methoxyphenyl)-2H-1-benzazepin-2-one A solution of 7-chloro-1,3,4,5-tetrahydro3-hydroxy-3-(methoxycarbonyl)-4-(4-methoxyphenyl)-2$\underline{H}$-1-benzazepin-2-one (0.5 g, 1.33 mmole) and lithium iodide (0.178 g, 1.33 mmole) in dry pyridine (20 ml) was refluxed under argon until complete conversion to product by TLC. The reaction was cooled to room temperature and concentrated in vacuo. The residue was dissolved in chloroform and extracted twice with 1N hydrochloric acid, once with saturated sodium chloride, and dried over magnesium sulfate. The solvent was removed in vacuo and the residue was triturated with ether to yield 0.22 g of the cis product.

(F)

(cis)-7-Chloro-3-hydroxy-1-[2-(dimethylamino)ethyl]-1,3,4,5-tetrahydro-4-(4-methoxyphenyl)-2H-1-benzazepin-2-one, monohydrochloride To a solution of (cis)-7-chloro-1,3,4,5-tetrahydro-3-hydroxy-4-(4-methoxyphenyl)-2H-1-benzazepin-2-(0.83 g, 2.612 mmole) in dry dimethylformamide (26.12 ml) was added a 60% dispersion of sodium hydride (0.11 g, 2.74 mmole). The reaction was stirred at room temperature under argon for 1 hour and a 1.7N solution of dimethylaminoethyl chloride in toluene (2.30 ml, 3.92 mmole) was added and stirred at 75° C. for 2 hours. The solvent was removed in vacuo and the residue was partitioned between ethyl acetate and 1N hydrochloric acid. The organic phase was washed with 1N hydrochloric acid, and dried over magnesium sulfate. The aqueous phase was treated with 6N sodium hydroxide to adjust to pH 11. The product was extracted three times with ethyl acetate and dried over magnesium sulfate. The solvent was removed in vacuo. The residue was dissolved in 2 ml of ethyl acetate and 5 ml of ether and treated with 1.2 equivalents of 1.39N hydrochloric acid in ether at 0° C. The solids were filtered and washed with ether to yield 0.65 g of the title compound.

(G)
(cis)-3-(Acetyloxy)-7-chloro-1-[2-(dimethylamino)ethyl]-1,3,4,5-tetrahydro-4-(4-methoxyphenyl)-2H-1-benzazepin-2-one, monohydrochloride A solution of (cis)-7-chloro-3-hydroxy-1-[2-(dimethylamino)ethyl]1,3,4,5-tetrahydro-4-(4-methoxyphenyl)-2H-1-benzazepin-2-one, monohydrochloride (0.62 g, 1.5 mmole) in dry acetic anhydride (25 ml) was heated at 110° C. under argon, until judged complete by TLC. The solvent was removed in vacuo and the residue was dissolved in ethyl acetate and 2 ml of saturated hydrochloric acid in ether was added. A white precipitate was filtered and dried (yield 0.5 g). The reaction was repeated to afford an additional 0.27 g of product. The batches were combined, melting point 207.5° C.–209° C.

Analysis Calc'd. for $C_{23}H_{28}N_2Cl_2O_4 \cdot 0.7$ mole $H_2O$: C, 57.55; H, 6.17; N, 5.84; Cl, 14.77 Found: C, 57.54; H, 5.86; N, 5.63; Cl, 14.92

METHOD II

Method II is identical with the above-described Method I except for the following parts D and E:

(D)
7-Chloro-1,3,4,5-tetrahydro-3-hydroxy-3-(methoxycarbonyl)-4-(4-methoxyphenyl)-2H-1-benzazepin-2-one A solution of 7-chloro-1,3,4,5-tetrahydro-3-(methoxycarbonyl)-4-(4-methoxyphenyl)-2H-1-benzazepin-2-one (15 g, 41.7 mmole) in 780 ml of tetrahydrofuran was cooled to −78° C. and 147 ml (167 mmole in tetrahydrofuran) of potassium hexamethyldisilazide solution was added. After stirring for 1 hour, 28.7 ml of triethyl phosphite (166.7 mmole) was added and anhydrous oxygen gas was rapidly bubbled through the resulting solution. The reaction temperature was then raised to 0° C. and allowed to stir for an additional hour. Oxygenation was then discontinued and the reaction was quenched by the addition of 50 ml of acetic acid. The reaction mixture was then concentrated and the residue dissolved in ethyl acetate. The organic solution was washed successively with 1N hydrochloric acid, saturated sodium bicarbonate, and brine and then dried over anhydrous sodium sulfate. Concentration of the dried organic solution afforded a solid which, upon trituration in hexane, gave 14.8 g of the title compound.

(E)
(cis)-7-Chloro-1,3,4,5-tetrahydro-3-hydroxy-4-(4-methoxyphenyl)-2H-1-benzazepin-2-one- A solution of 7-chloro-1,3,4,5-tetrahydro-3-hydroxy-3-(methoxycarbonyl)-4-(4-methoxyphenyl)-2H-1-benzazepin-2-one (16.4 g, 43.7 mmole) and lithium iodide (23.7 g, 174.6 mmole) in 290 ml of pyridine containing 1% water was refluxed under argon until complete conversion to product by TLC (ca. 1.5 hours). The reaction was cooled to room temperature and concentrated in vacuo. The residue was dissolved in ethyl acetate and extracted with 1N hydrochloric acid, saturated sodium bicarbonate and saturated sodium chloride. The solution was dried over magnesium sulfate and concentrated. The residue was recrystallized from ethyl acetate to afford 6.8 g of pure cis product.

EXAMPLE 2

(cis)-3-(Acetyloxy)-1-[2-(dimethylamino)ethyl]-1,3,4,5-tetrahydro-4-(4-methoxyphenyl)-2H-1-benzazepin-2-one, monohydrochloride (A)
[1-(4-Methoxyphenyl)-2-(2-nitrophenyl)ethyl]-propanedioic acid, dimethyl ester Dimethyl p-methoxybenzylidene malonate (90 g, 360 mmol) was dissolved in 700 ml of dry dimethylformamide under argon and 21.6 g (540 mmol) of sodium hydride as a 60% dispersion in oil was added. The suspension was then treated at room temperature with 33.9 ml (400 mmol) of 2-nitrotoluene and a catalytic amount of t-butanol was added. After stirring for 16 hours, the reaction was quenched by the addition of 3 L of 1N hydrochloric acid and extracted four times with ether. The combined organic phases were dried over sodium sulfate and evaporated to yield 171 g of dark oil. Chromatography on 1.5 kg of 60–200 silica with 4:1 hexane-ethyl acetate gave 22 g of high purity product and an additional 22 g of somewhat impure material as judged by tlc analysis.

(B)
[2-(2-Aminophenyl)-1-(4-methoxyphenyl)ethyl]-propanedioic acid, dimethyl ester Hydrogenation of 22 g of [1-(4-methoxyphenyl)-2-(2-nitrophenyl)ethyl]propanedioic acid, dimethyl ester in 450 ml of 5:1 methanol-acetic acid at atmospheric pressure for 16 hours followed by recrystallization of the crude product from isopropanol gave 13 g of the desired product. Chromatography of the concentrated mother liquor on LPS-1 silica with 7:3 hexane-ethyl acetate gave an additional 2.24 g of product.

(C)
1,3,4,5-tetrahydro-3-(Methoxycarbonyl)-4-(4-methoxyphenyl)-2H-1-benzazepin-2-one A solution containing 11.97 (33.5 mmol) of [2-(2-aminophenyl)-1-(4-methoxyphenyl)ethyl]propanedioic acid, dimethyl ester and 9.2 ml of 25% sodium methoxide (40.2 mmol) in 80 ml of methanol was refluxed for 1.5 hours and cooled to room temperature. Excess 1M hydrochloric acid solution was then added and the resulting precipitated product was removed by filtration to give 9.18 g of pure material, melting point 217°–219° C.

(D)
1,3,4,5-tetrahydro-3-Hydroxy-3-(methoxycarbonyl)-4-(4-methoxyphenyl)-2H-1-benzazepin-2-one Dry oxygen gas was bubbled through a cooled (ice bath) solution of 1,3,4,5-tetrahydro-3-(methoxycarbonyl)-4-(4-methoxyphenyl)-2H-1-benzazepin-2-one (13 g, 40.2 mmol) in 130 ml of dry tetrahydrofuran for 30 minutes. Potassium hexamethyldisilazide in toluene (180 ml, 0.67M, 120.5 mmol) was then added over a 7 minute period under a continuous stream of oxygen. After stirring for 2.5 hours, the oxygen flow was terminated and the reaction was quenched by the addition of 200 ml of 5% potassium bisulfate. Solid sodium sulfite (15 g) was then added followed by the addition of 100 ml of methanol and the mixture was stirred for an additional 30 minutes. The mixture was then extracted twice with ethyl acetate and the combined organic layers were washed three times with 1M hydrochloric acid, once with saturated bicarbonate solution followed by brine and then dried over sodium sulfate. Concentration afforded 15 g of crude product which was triturated with ether-hexane to yield 9.3 g of high purity product.

(E)

(cis)-1,3,4,5-tetrahydro-3-Hydroxy-4-(4-methoxyphenyl)-2H-1-benzazepin-2-one

A solution containing 5.26 g (14.6 mmol) of 1,3,4,5-tetrahydro-3-hydroxy-3-(methoxycarbonyl)-4-(4-methoxyphenyl)-2H-1-benzazepin-2-one and 19. (147 mmol) of anhydrous lithium iodide in 150 ml of dry pyridine was refluxed for one hour. After concentration, the crude product was dissolved in ethyl acetate, washed with 6M hydrochloric acid followed by saturated bicarbonate and dried over sodium sulfate. Concentration followed by trituration with ether gave 2.81 g of essentially pure cis isomer, melting point 173.5°–175.5° C. (dec).

(F)

(cis)-3-Hydroxy-1-[2-(dimethylamino)ethyl]-1,3,4,5-tetrahydro-4-(4-methoxyphenyl)-2H-1-benzazepin-2-one, monohydrochloride A solution containing 1.0 g of (cis)-1,3,4,5-tetrahydro-3-hydroxy-4-(4-methoxyphenyl)-2H-1-benzaze dimethylformamide was treated with 0.15 g (3.71 mmol) of sodium hydride as a 60% dispersion in oil and stirred for one hour. A solution of N,N-dimethyl-2-chloroethyl amine in toluene (3.1 ml of 1.7M solution, 5.3 mmol) was then added and the mixture was heated at 75° C. for 1.5 hours. The reaction was then concentrated on a vacuum pump ahd the residue was partitioned between ethyl acetate and 1M hydrochloric acid. The organic phase was washed twice more with the aqueous hydrochloric acid and the combined aqueous phases were adjusted to pH 11 and extracted three times with ethyl acetate. The combined ethyl acetate layers were dried over sodium sulfate and concentrated to yield 1.17 g of the desired material. The crude product was dissolved in a minimal amount of chloroform and acidified at 0° C. with saturated ether/hydrogen chloride solution resulting in the formation of 1.27 g of an off-white powder.

(G)

(cis)-3-(Acetyloxy)-1-[2-(dimethylamino)ethyl]-1,3,4,5-tetrahydro-4-(4-methoxyphenyl)-2H-1-benzazepin-2-one, monohydrochloride (cis)-3-Hydroxy-1-[2-(dimethylamino)ethyl]-1,3,4,5-tetrahydro-4-(4-methoxyphenyl)-2H-1-benzazepin-2-one, monohydrochloride (1.27 g, 2.83 mmol) was slurried in 28 ml of acetic anhydride and heated at 100° C. under argon for 3 hours. The resulting solution was then concentrated and the residue dissolved in ethyl acetate. After crystallization commenced, hydrogen chloride saturated ether was added and the mixture was filtered to afford 1.25 g of the desired material as an off-white powder, melting point 215°–216° C.

Analysis Calc'd. for $C_{23}H_{29}ClN_2O_4$ 0.4 mole $H_2O$: C, 62.76; H, 6.82; N, 6.36; Cl, 8.05 Found: C, 62.76; H, 6.65; N, 6.40; Cl, 7.97

EXAMPLE 3

(trans)-3-(Acetyloxy)-1-[2-(dimethylamino)ethyl]-1,3,4,5-tetrahydro-4-(4-methoxyphenyl)-2H-1-benzazepin-2-one, monohydrochloride (A)

(trans)-3-Hydroxy-1,3,4,5-tetrahydro-4-(4-methoxyphenyl)-2H-1-benzazepin-2-one

Flash chromatography (LPS-1 silica gel, 70:30 hexanes-ethyl acetate) of the mother liquor resulting from the trituration from ether of the crude (cis)-3-hydroxy-1,3,4,5-tetrahydro-4-(4-methoxyphenyl)-2H-1-benzazepin-2-one (see example 2E) afforded the title trans isomer, melting point 168°–170° C.

(B)

(trans)-3-Hydroxy-1-[2-(dimethylamino)ethyl]-1,3,4,5-tetrahydro-4-(4-methoxyphenyl)-2H-1-benzazepin-2-one Following the procedure of example 2F, but substituting 0.57 g (2.01 mmol) of (trans)-3-hydroxy-1,3,4,5-tetrahydro-4-(4-methoxyphenyl)-2H-1-benzazepin-2-one for the corresponding cis isomer, yielded 0.66 g of the title compound as an oil.

(C)

(trans)-3-(Acetyloxy)-1-[2-(dimethylamino)ethyl]-1,3,4,5-tetrahydro-4-(4-methoxyphenyl)-2H-1-benzazepin-2-one, monohydrochloride Following the procedure of example 2G, but substituting 0.654 g (1.83 mmol) of (trans)-3-hydroxy-1-[2-(dimethylamino)ethyl]-1,3,4,5-tetrahydro-4-(4-methoxyphenyl)-2H-1-benzazepin-2-one for the monohydrochloride salt of the corresponding cis isomer yielded 0.5 g of the title compound as a white crystalline solid after trituration from ethyl acetate and recrystallization from methanol/isopropanol. The product melted at 254°–256.5° C.

Analysis Calc'd for $C_{23}H_{29}ClN_2O_4$ 0.2 mole of $H_2O$: C, 63.31; H, 6.79; N, 6.42; Cl, 8.12 Found: C, 63.31; H, 6.90; N, 6.29; Cl, 8.13

EXAMPLES 4–8

Following the procedure of Example 1, Method II, but substituting the compound listed in Column I for dimethyl p-methoxybenzylidene malonate, yielded the compound listed in Column II.

| Column I | Column II |
| --- | --- |
| 4. dimethyl p-(trifluoromethyl)-benzylidene malonate | (cis)-3-(Acetyloxy)-7-chloro-1-[2-(dimethylamino)-ethyl]-1,3,4,5-tetrahydro-4-[4-(trifluoromethyl)-phenyl]-2H—1-benzazepin-2-one, monohydrochloride, melting point 225.5–227° C., dec. |
| 5. dimethyl benzylidene malonate | (cis)-3-(Acetyloxy)-7-chloro-1-[2-(dimethylamino)ethyl]-1,3,4,5-tetrahydro-4-phenyl-2H—1-benzazepin-2-one, monohydrochloride, melting point 247–250° C., dec. |
| 6. dimethyl o-methoxybenzylidene malonate | (cis)-3-(Acetyloxy)-7-chloro-1-[2-(dimethylamino)ethyl]-1,3,4,5-tetrahydro-4-(2-methoxyphenyl)-2H—1-benzazepin-2-one, monohydrochloride, melting point 250–252° C., dec. |
| 7. dimethyl m-methoxy- | (cis)-3-(Acetyloxy)-7-chloro- |

| Column I | Column II |
|---|---|
| benzylidene malonate | 1-[2-(dimethylamino)ethyl]-1,3,4,5-tetrahydro-4-(3-methoxyphenyl)-2H—1-benzazepin-2-one, monohydrochloride, melting point 225–226° C. |
| 8. dimethyl p-chloro-benzylidene malonate | (cis)-3-(Acetyloxy)-7-chloro-4-(4-chlorophenyl)-1-[2-(dimethylamino)ethyl]-1,3,4,5-tetrahydro-2H—1-benzazepin-2-one, methanesulfonate (1:1) salt, melting point 250–250.5° C. |

EXAMPLES 9–22

Following the procedure of Example 1, Method II, but substituting the compound listed in Column I for 5-chloro-2-nitrotoluene, yielded the compound listed in Column II.

| Column I | Column II |
|---|---|
| 9. 6-methyl-2-nitro-toluene | (cis)-3-(Acetyloxy)-1-[2-(dimethylamino)ethyl]-1,3,4,5-tetrahydro-4-(4-methoxyphenyl)-6-methyl-2H—1-benzazepin-2-one, monohydrochloride, melting point 176–178° C. (sintering at 172° C.). |
| 10. 6-chloro-2-nitrotoluene | (cis)-3-(Acetyloxy)-6-chloro-1-[2-(dimethylamino)ethyl]-1,3,4,5-tetrahydro-4-(4-methoxyphenyl)-2H—1-benzazepin-2-one, monohydrochloride, melting point 151–153° C., sintering at 148° C. |
| 11. 4-chloro-2-nitrotoluene | (cis)-3-(Acetyloxy)-8-chloro-1-[2-(dimethylamino)ethyl]-1,3,4,5-tetrahydro-4-(4-methoxyphenyl)-2H—1-benzazepin-2-one, monohydrochloride, melting point 173–176° C., sintering at 164° C. |
| 12. 5-(phenylmethoxy)-2-nitrotoluene | (cis)-3-(Acetyloxy)-1-[2-(dimethylamino)ethyl]-1,3,4,5-tetrahydro-4-(4-methoxyphenyl)-7-(phenylmethoxy)-2H—1-benzazepin-2-one, monohydrochloride, melting point 117–120° C., sintering at 107° C. |
| 13. 5-(cyclohexylmethoxy)-2-nitrotoluene | (cis)-3-(Acetyloxy)-1-[2-(dimethylamino)ethyl]-1,3,4,5-tetrahydro-4-(4-methoxyphenyl)-7-(cyclohexylmethoxy)-2H—1-benzazepin-2-one, monohydrochloride, melting point 197–200° C. (dec), sintering at 186° C. |
| 14. 5-(difluoromethoxy)-2-nitrotoluene | (cis)-3-(Acetyloxy)-1-[2-(dimethylamino)ethyl]-1,3,4,5-tetrahydro-4-(4-methoxyphenyl)-7-(difluoromethoxy)-2H—1-benzazepin-2-one, monohydrochloride, melting point 206–208° C. (dec), sintering at 170° C. |
| 15. 5-(2,2,2-trifluoroethoxy)-2-nitrotoluene | (cis)-3-(Acetyloxy)-1-[2-(dimethylamino)ethyl]-1,3,4,5-tetrahydro-4-(4-methoxyphenyl)-7-(2,2,2-trifluoroethoxy)-2H—1-benzazepin-2-one, monohydrochloride, melting point 211–213° C. |
| 16. 5-phenoxy-2-nitrotoluene | (cis)-3-(Acetyloxy)-1-[2-(dimethylamino)ethyl]-1,3,4,5-tetrahydro-4-(4-methoxyphenyl)-7-phenoxy-2H—1-benzazepin-2-one, monohydrochloride, melting point 155° C. (dec). |
| 17. 6-cyano-2-nitro-toluene | (cis)-3-(Acetyloxy)-1-[2-(dimethylamino)ethyl]-1,3,4,5-tetrahydro-4-(4-methoxyphenyl)-6-cyano-2H—1-benzazepin-2-one, monohydrochloride, melting point 200–202° C. (dec), sintering at 198° C. |
| 18. 5-(phenylthio)-2-nitrotoluene | (cis)-3-(Acetyloxy)-1-[2-(dimethylamino)ethyl]-1,3,4,5-tetrahydro-4-(4-methoxyphenyl)-7-(phenylthio)-2H—1-benzazepin-2-one, monohydrochloride, melting point 193–195° C. (dec). |
| 19. 5-[(1,1-dimethylethyl)thio]-2-nitrotoluene | (cis)-3-(Acetyloxy)-1-[2-(dimethylamino)ethyl]-1,3,4,5-tetrahydro-4-(4-methoxyphenyl)-7-[(1,1-dimethylethyl)thio]-2H—1-benzazepin-2-one, monohydrochloride, melting point 190–214° C. (dec). |
| 20. 5-(methylthio)-2-nitrotoluene | (cis)-3-(Acetyloxy)-1-[2-(dimethylamino)ethyl]-1,3,4,5-tetrahydro-4-(4-methoxyphenyl)-7-(methylthio)-2H—1-benzazepin-2-one, monohydrochloride, melting point 235° C. (dec). |
| 21. 5-ethoxy-2-nitro-toluene | (cis)-3-(Acetyloxy)-1-[2-(dimethylamino)ethyl]-1,3,4,5-tetrahydro-4-(4-methoxyphenyl)-7-ethoxy-2H—1-benzazepin-2-one, monohydrochloride, melting point 224–226° C., sintering at 216° C. |
| 22. 5-(diphenylmethoxy)-2-nitrotoluene | (cis)-3-(Acetyloxy)-1-[2-(dimethylamino)ethyl]-1,3,4,5-tetrahydro-4-(4-methoxyphenyl)-7-(diphenylmethoxy)-2H—1-benzazepin-2-one, monohydrochloride, melting point 145–147° C. (dec), sintering at 140° C. |

EXAMPLE 23

(cis)-3-(Acetyloxy)-1-[2-(dimethylamino)ethyl]-1,3,4,5-tetrahydro-7-hydroxy-4-(4-methoxyphenyl)-2H-1-benzazepin-2-one, monohydrochloride A solution of 0.5 g (0.87 mmol) of (cis)-3-(acetyloxy)-1-[2-(dimethylamino)ethyl]-1,3,4,5-tetrahydro-4-(4-methoxyphenyl)-7-(phenylmethoxy)-2H-1-benzazepin-2-one, monohydrochloride, (see Example 12) in 30 ml of methanol was treated under argon with 150 mg of 10% palladium on charcoal and shaken on the Parr hydrogenator at 50 p.s.i. for 5 hours. The catalyst was filtered off under argon, washed with methanol and the combined filtrates evaporated. The residue (which began to solidify) was rubbed under ether and the evaporation repeated. The solid was dried in vacuo for several hours yielding 0.40 g of the title compound, melting point 229°–231° C., dec., preceded by gradual sintering.

Analysis calc'd. for $C_{23}H_{28}N_2O_5 \cdot HCl \cdot 1.5MH_2O$: C, 58.04; H, 6.58; N, 5.89; Cl, 7.45 Found: C, 58.29; H, 6.33; N, 5.70; Cl, 7.63

EXAMPLE 24

(cis)-7-Chloro-3-[(2-chloro-4-nitrobenzoyl)oxy]-1-[2-(dimethylamino)ethyl]-1,3,4,5-tetrahydro-4-(4-methoxyphenyl)-2H-1-benzazepin-2-one, methanesulfonate (1:1) salt A solution of 0.80 g (2.06 mmol) of (cis)-7-chloro-3-hydroxy-1-[2-(dimethylamino)ethyl]-1,3,4,5-tetrahydro-4-(4-methoxyphenyl)-2H-1-benzazepin-2-one (see Example 1F) was treated with 0.65 g (3.2 mmol) of 2-chloro-4-nitrobenzoic acid, 0.52 g (2.5 mmol) of dicyclohexylcarbodiimide and 0.04 g of 4-dimethylaminopyridine. A precipitate of dicyclohexylurea separated from solution. After standing overnight at room temperature, the reaction was filtered. The filtrate was extracted with 10 ml of 10% potassium carbonate, 5 ml of 5% potassium carbonate (twice), 5 ml of water and 5 ml of saturated sodium chloride solution. The organic phase was dried (magnesium sulfate), filtered and the solvent evaporated to give 1.3 g of a pale yellow solid. The mixture was purified by chromatography on 50 g of silica gel using 1:1 dichloromethane-ethyl acetate as the solvent to give 1.0 g of the cis ester containing a small amount of the trans ester. The mixture was suspended in 5 ml of ether, cooled and filtered to give 0.9 g of nearly colorless solid. The small quantity of the trans ester still present was removed by suspending and stirring in 3 ml of isopropanol for 1 hour at room temperature, filtering and washing with isopropanol and ether to give 0.76 g of the free base, melting point 164°–166° C. The material was converted to the methanesulfonate salt by dissolving it in 10 ml of warm ethyl acetate and treating with a solution of 0.135 g of methanesulfonic acid in 5 ml of ethyl acetate. The resulting solution was gradually diluted with ether to give a colorless crystalline product. After cooling overnight, the solid was filtered, washed with ether and dried; weight 0.84 g, melting point 215°–217° C.

Analysis Calc'd. for $C_{28}H_{27}N_3Cl_2O_6 \cdot CH_3SO_3H$: C, 52.09; H, 4.67; N, 6.28; Cl, 10.61; S, 4.8. Found: C, 51.87; H, 4.62; N, 6.14; Cl, 10.59; S, 4.81.

EXAMPLE 25

(cis)-7-Chloro-1-[2-(dimethylamino)ethyl]-2,3,4,5-tetrahydro-4-(4-methoxyphenyl)-2-oxo-1H-1-benzazepin-3-yl methylcarbamate, monohydrochloride A stirred suspension of 0.80 g (2.06 mmole) of (cis)-7-chloro-3-hydroxy-1-[2-(dimethylamino)ethyl]-1,3,4,5-tetrahydro-4-(4-methoxyphenyl)-2H-1-benzazepin-2-one (see Example 1F) in 6 ml of dichloromethane was treated with 1.2 g (21 mmole) of methyl isocyanate and the resulting solution was allowed to stand at room temperature for 22 hours. TLC indicated the presence of a small quantity of starting material. The mixture was treated with 6 ml of acetonitrile and 1.2 g of methyl isocyanate and allowed to stand at room temperature for 20 hours. The solution was concentrated to give 1.1 g of a solid, which was dissolved in 35 ml of ethyl acetate, extracted with 5 ml of water (twice), dried over magnesium sulfate, filtered and the solvent evaporated to give 0.93 g of solid. This material was suspended in 5 ml of hexane and filtered to give 0.79 g of solid. This material was suspended in 5 ml of ether, cooled and filtered to give 0.62 g of solid. This material was dissolved in 3 ml of ethanol and treated with 0.26 ml of 5.7N ethanolic hydrogen chloride and gradually diluted with about 50 ml of ether to give a crystalline product weighing 0.61 g, melting point 238°–240° C., dec.

Analysis calc'd. for $C_{23}H_{28}N_3ClO_4 \cdot HCl \cdot H_2O$: C, 56.21; H, 6.15; N, 8.55; Cl, 14.43 Found: C, 56.42; H, 6.14; N, 8.58; Cl, 14.48

EXAMPLE 26

(d-cis)-3-(Acetyloxy)-7-chloro-1-[2-(dimethylamino)ethyl]-1,3,4,5-tetrahydro-4-(4-methoxyphenyl)-2H-1-benzazepin-2-one, monohydrochloride (A)

(d-cis)-3-(Hydroxy)-7-chloro-1-[2-(dimethylamino)ethyl]-1,3,4,5-tetrahydro-4-(4-methoxyphenyl)-2H-1-benzazepin-2-one A mixture of 4.50 g (1.6 mmol) of (d,l-cis)-3-(hydroxy)-7-chloro-1-[2-(dimethylamino)ethyl]-1,3,4,5-tetrahydro-4-(4-methoxyphenyl)-2H-1-benzazepin-2-one (crystallized from acetonitrile; see Example 1F) and 1.74 g (11.6 mmol) of d(+) tartaric acid in 225 ml of methanol was heated and the hot solution was seeded and allowed to crystallize at room temperature for 2 days. The mother liquor was decanted from the crystalline solid and the latter rinsed with fresh methanol. After removal of adhering solvent, the solid weighed 3.22 g $[\alpha]_D + 63.1°$ (c, 1% acetic acid). The latter was dissolved in 85 ml of hot methanol, seeded and allowed to stand at room temperature for 3 days to give 2.16 g of colorless product $[\alpha]_D + 106°$ (c, 1% acetic acid). After recrystallization from 65 ml of hot methanol, the solid weighed 1.67 g; melting point 195°–197° C. (dec.), sintering at 190° C.; $[\alpha]_D + 119°$ (c, 1% acetic acid). The 1.67 g of material was combined with 0.60 g of product (from 2.0 g of d-l mixture), suspended in a stirred mixture of 70 ml of water and 70 ml of dichloromethane and treated portionwise with 8.1 ml of N sodium hydroxide. The layers were separated and the aqueous phase was extracted with 50 ml of dichloromethane (twice). The organic phases were combined, washed with 20 ml of water, dried (magnesium sulfate), filtered and the solvent evaporated to give 1.49 g of colorless solid, melting point 55°–60° C. (s, 50° C.), $[\alpha]_D + 194°$ (c, 1% chloroform). $R_f$ 0.28 (8:1:1 dichloromethane-methanol-acetic acid).

(B)

(d-cis)-3-(Acetyloxy)-7-chloro-1-[2-(dimethylamino)ethyl]-1,3,4,5-tetrahydro-4-(4-methoxyphenyl)-2H-1-benzazepin-2-one, monohydrochloride A solution of 1.48 g (3.8 mmol) of (d-cis)-3-(hydroxy)-7-chloro-1-[2-(dimethylamino)ethyl]-1,3,4,5-tetrahydro-4-(4-methoxyphenyl)-2H-1-benzazepin-2-one in 25 ml of ethanol was treated with 0.68 ml of 5.7N hydrogen chloride in ethanol. This solution was concentrated on a rotary evaporator to give 1.71 g of the hydrochloride salt as a colorless solid. $[\alpha]_D + 143°$ (c, 1% methanol). This material was dissolved in 50 ml of acetic anhydride and heated in an oil bath at 110°–120° C. for 3 hours. The starting material initially crystallized from solution and redissolved when the bath temperature reached 110° C. TLC indicated the reaction was essentially complete after 2 hours. The solution was concentrated on a rotary evaporator to give a colorless solid. The latter was suspended in 25 ml of ethyl acetate, diluted with 25 ml of ether and allowed to stand at room temperature for 2 hours. The solid was filtered, washed with ether and dried in vacuo to give 1.65 g of material, melting point 252°–254° C. (dec), $[\alpha]_D + 131°$ (c, 1% methanol). R$_f$ 0.41 (8:1:1 dichloromethane-methanol-acetic acid).

Analysis Calc'd. for C$_{23}$H$_{27}$ClN$_2$O$_4$.HCl.0.5H$_2$O: C, 57.95; H, 6.13; N, 5.87; Cl, 14.88 Found: C, 57.95; H, 5.98; N, 5.68; Cl, 14.62

EXAMPLE 27

(l-cis)-3-(Acetyloxy)-7-chloro-1-[2-(dimethylamino)ethyl]-1,3,4,5-tetrahydro-4-(4-methoxyphenyl)-2H-1-benzazepin-2-one, monohydrochloride (A)

(l-cis)-3-(Hydroxy)-7-chloro-1-[2-(dimethylamino)ethyl]-1,3,4,5-tetrahydro-4-(4-methoxyphenyl)-2H-1-benzazepin-2-one The mother liquor from Example 26 was concentrated on the rotary evaporator to give 3.35 g of colorless solid, [α]$_D$−41.5° (c, 1% acetic acid). This solid was converted to the free base by suspending in a stirred mixture of 100 ml of water and 150 ml of dichloromethane and adding 9 ml of N sodium hydroxide (portionwise). The layers were separated and the aqueous phase was extracted with 60 ml of dichloromethane (twice). The organic phases were combined, extracted with 20 ml of water, dried (magnesium sulfate), filtered and the solvent evaporated to give 2.35 g of solid (free base), [α]$_D$−73.7° (c, 1% chloroform). A suspension of this material, 0.90 g of l(−)tartaric acid and 115 ml of methanol was heated and the hot solution seeded and allowed to crystallize at room temperature for 3 days. The crystalline material was filtered and washed with methanol to give 1.82 g of colorless product, [α]$_D$−118° (c, 1% acetic acid). After recrystallization from 50 ml of methanol at room temperature, the salt weighed 1.59 g, [α]$_D$−117° (c, 1% acetic acid), melting point 198°–200° (dec). This material was combined with 0.64 g of product (from 2.0 g of the d-l mixture) and converted to the free base in the manner described above to give 1.58 g of colorless solid, melting point 55°–60° C. (s. 50° C.), [α]$_D$−202° (c, 1% chloroform). R$_f$ 0.28 (8:1:1 dichloromethane-methanol-acetic acid).

(B)

(l-cis)-3-(Acetyloxy)-7-chloro-1-[2-(dimethylamino)ethyl]-1,3,4,5-tetrahydro-4-(4-methoxyphenyl)-2H-1-benzazepin-2-one, monohydrochloride A solution of 1.45 g (3.7 mmol) of (l-cis)-3-(hydroxy)-7-chloro-1-[2-(dimethylamino)ethyl]-1,3,4,5-tetrahydro-4-(4-methoxyphenyl)-2H-1-benzazepin-2-one in 25 ml of ethanol was treated with 0.68 ml of 5.7N hydrogen chloride in ethanol. This solution was concentrated on a rotary evaporator to give 1.74 g of the hydrochloride salt as a colorless solid, [α]$_D$−144° (c, 1% methanol). This material was acetylated in the manner described in Example 26 part B to give 1.70 g of colorless solid, melting point 253°–255° C. (dec), [α]$_D$−130° (c, 1% methanol). R$_f$ 0.41 (8:1:1 dichloromethane-methanol-acetic acid).

Analysis Calc'd. for C$_{23}$H$_{27}$ClN$_2$O$_4$.HCl.0.5H$_2$O: C, 57.95; H, 6.13; N, 5.87; Cl, 14.88 Found: C, 57.93; N, 5.94; N, 5.72; Cl, 14.75

EXAMPLE 28

(cis)-3-(Acetyloxy)-1-[2-(dimethylamino)ethyl]-1,3,4,5-tetrahydro-4-(4-methoxyphenyl)-7-(trifluoromethyl)-2H-1-benzazepin-2-one, monohydrochloride (A)

[2-(5-Trifluoromethyl-2-nitrophenyl)-1-(4-methoxyphenyl)ethyl]propanedioic acid, dimethyl ester To a 2 liter three-neck flask (under nitrogen) was added 67.0 g (0.293 mol) of dimethyl p-methoxybenzylidene malonate and 450 ml of dimethylformamide. The stirred solution was treated with 18.7 g (0.39 mole) of 50% sodium hydride dispersion. This mixture was treated dropwise with a solution of 60.5 g (0.293 mol) of 2-nitro-5-(trifluoromethyl)toluene in 50 ml of dimethylformamide, over a period of 1 hour while maintaining the temperature at 28°–32° C. (near the end of the addition, the temperature rose to 38° C. and was rapidly cooled to 30° C.). This mixture was stirred for 4 hours at room temperature, cooled, treated portionwise with 25 ml of acetic acid and poured onto 2.5 liters of ice water. The mixture was extracted with 250 ml of dichloromethane (3 times). The organic phases were combined, washed with 500 ml of water (3 times), dried (magnesium sulfate), filtered and the solvent evaporated to give 126 g of a pale brown semi-solid. The latter was dissolved in 270 ml of methanol, cooled and filtered to give 72.8 g of a pale yellow product, melting point 110°–112° C. R$_f$=0.74 (1:1 ethyl acetate-hexane). A sample recrystallized from methanol, melted at 111°–113° C.

(B)

[2-(5-Trifluoromethyl-2-aminophenyl)-1-(4-methoxyphenyl)ethyl]propanedioic acid, dimethyl ester A suspension of 25.0 g (0.055 mol) of [2-(5-trifluoromethyl-2-nitrophenyl)-1-(4-methoxyphenyl)ethyl]propanedioic acid, dimethyl ester in 200 ml of methanol was treated with a cold suspension of 2.5 g of 5% palladium on charcoal in 50 ml of methanol (under nitrogen) and placed on the Parr apparatus at 58 psi of hydrogen. After 30 minutes, the mixture was heated to 50°–55° C. for 1 hour to assure that all of the nitro compound had dissolved. The mixture was removed from the Parr and allowed to stand at room temperature overnight. The flask was heated to dissolve the crystallized product, and the hot solution was filtered through Celite (under nitrogen) and washed with hot methanol. The colorless filtrate was concentrated on a rotary evaporator to give 22.2 g of a nearly colorless solid. The latter was triturated with 100 ml of hexane and then with 50 ml of hexane. The solvent was decanted and the entrained solvent removed on a rotary evaporator to give 21.3 g of product, melting point 124°–127° C. R$_f$=0.62 (1:1 ethyl acetate-hexane). A sample of this material, after crystallization from methanol, melted at 125°–127° C.

(C)

7-(Trifluoromethyl)-1,3,4,5-tetrahydro-3-(methoxycarbonyl)-4-(4-methoxyphenyl)-2H-1-benzazepin-2-one Cyclization of 20.0 g (0.047 mol) of [2-(5-trifluoromethyl-2-aminophenyl)-1-(4-methoxyphenyl)ethyl]propanedioic acid, dimethyl ester in 200 ml of methanol with 13.3 ml of 25% sodium methoxide following the procedure of Example 1, Method I, part C gave 19.0 g of a pale yellow foam-like material. The latter was suspended in 30 ml of isopropyl alcohol, allowed to stand for 1 hour, filtered and washed with isopropyl alcohol and hexane; yield 13.64 g melting point 161°–163° C. $R_f$=0.30 (1:1 ethyl acetate-hexane). Concentration of the isopropyl alcohol filtrate gave an additional 0.8 g of colorless product, melting point 161°–163° C.

(D)

7-(Trifluoromethyl)-1,3,4,5-tetrahydro-3-hydroxy-3-(methoxycarbonyl)-4-(4-methoxyphenyl)-2H-1-benzazepin-2-one 7-(Trifluoromethyl)-1,3,4,5-tetrahydro-3-(methoxycarbonyl)-4-(4-methoxyphenyl)-2H-1-benzazepin-2-one (7.0 g; 0.0178 mol) in 330 ml of tetrahydrofuran was treated with 64 ml (0.072 mol) of 1.125M potassium hexamethyldisilazide in tetrahydrofuran, then with 12.4 ml (0.0723 mol) of triethyl phosphite, and finally with oxygen for 2 hours as described in Example 1, Method II, part D, to give 7.0 g of pale cream-colored solid (following trituration with 200 ml of hexane); melting point 196°–198° C. (dec.), s. 192° C. TLC: $R_f$=0.24 (1:1 ethyl acetate-hexane).

(E)

7-(Trifluoromethyl)-1,3,4,5-tetrahydro-3-hydroxy-4-(4-methoxyphenyl)-2H-1-benzazepin-2-one Interaction of 7-(trifluoromethyl)-1,3,4,5-tetrahydro-3-hydroxy-3-(methoxycarbonyl)-4-(4-methoxyphenyl)-2H-1-benzazepin-2-one (6.8 g; 0.0166 mol) and 5.8 g (0.0433 mol) of lithium iodide in 250 ml of pyridine as described in Example 1, Method II, part E (refluxed 2 hours) gave 5.53 g of crude solid which was triturated with 120 ml of ether and cooled to yield 4.45 g of colorless material; melting point 204°–206° C. (s. 201° C.). TLC (1:1 ethyl acetate-hexane) showed an approximate 60:40 ratio of cis and trans products.

(F)

(cis)-3-(Hydroxy)-1-[2-(dimethylamino)ethyl]-1,3,4,5-tetrahydro-4-(4-methoxyphenyl)-7-(trifluoromethyl)-2H-1-benzazepin-2-one, monohydrochloride 7-(Trifluoromethyl)-1,3,4,5-tetrahydro-3-hydroxy-4-(4-methoxyphenyl)-2H-1-benzazepin-2-one (2.75 g; 7.83 mmol) was treated in 85 ml of dimethylformamide with 0.35 g (8.75 mmol) of 60% sodium hydride, then with 5.4 ml of 2.15N dimethylaminoethyl chloride in toluene as described in Example 1, Method I, part F to give 3.07 g of a mixture of cis and trans bases. Chromatography on 110 g of Baker silica gel eluting with 94:6 dichloromethane-methanol yielded 0.80 g of the cis isomer (60:40 mixture of isomers). This was combined with 0.55 g of chromatographed product from an earlier experiment by dissolving in methanol-chloroform, treated with 0.62 ml of 5.75N ethanolic hydrogen chloride, and the solvent removed on a rotary evaporator. The sticky residue was rubbed under ether (became amorphous), and the evaporation repeated. After drying at 0.2 mm for several hours, the material weighed 1.58 g. TLC: $R_f$=0.31 (8:1:1 dichloromethane-methanol-acetic acid). Additional product (together with trans isomer) was found in later fractions.

(G)

(cis)-3-(Acetyloxy)-1-[2-(dimethylamino)ethyl]-1,3,4,5-tetrahydro-4-(4-methoxyphenyl)-7-(trifluoromethyl)-2H-1-benzazepin-2-one, monohydrochloride A stirred suspension of (cis)-3-(hydroxy)-1-[2-(dimethylamino)ethyl]-1,3,4,5-tetrahydro-4-(4-methoxyphenyl)-7-(trifluoromethyl)-2H-1-benzazepin-2-one, monohydrochloride (1.50 g; 3.27 mmol) in 50 ml of acetic anhydride was heated in an oil bath at 110°–117° C. (solution obtained) for 2.5 hours (under argon). TLC (8:1:1 dichloromethane-methanol-acetic acid) showed the reaction to be complete. The acetic anhydride was removed on a rotary evaporator at 0.2 mm to give a solid. The latter was rubbed under ethyl acetate, 1 ml of saturated hydrogen chloride in ether (to pH 2) was added and the evaporation repeated. The colorless material was rubbed under ether, cooled overnight, filtered, washed in ether, and dried in vacuo; yield 1.43 g; melting point 230°–232° C. (dec.); s. 227° C. TLC: $R_f$=0.41 (8:1:1 dichloromethane-methanol-acetic acid).

Analysis Calc'd. for $C_{24}H_{27}F_3N_2O_4 \cdot HCl \cdot 0.5H_2O$: C, 56.52; H, 5.73; N, 5.49; Cl, 6.95; F, 11.18 Found: C, 56.31; H, 5.57; N, 5.46; Cl, 6.81; F, 11.29

EXAMPLE 29

(cis)-3-(Acetyloxy)-1-[2-(dimethylamino)ethyl]-1,3,4,5-tetrahydro-4-(4-methoxyphenyl)-6-(trifluoromethyl)-2H-1-benzazepin-2-one, monohydrochloride (A)

[2-(6-Trifluoromethyl-2-nitrophenyl)-1-(4-methoxyphenyl)ethyl]propanedioic acid, dimethyl ester To a dry 2 liter three-neck flask equipped with a stirrer, thermometer, condenser and dropping funnel was added 52.7 g (0.21 ml) of dimethyl p-methoxybenzylidene malonate and 350 ml of dimethylformamide. This solution was stirred (under nitrogen), treated with 11.0 g (0.27 mole) of 60% sodium hydride dispersion and this slurry was treated dropwise with a solution of 43.0 g (0.21 mol) of 2-nitro-6-(trifluoromethyl)toluene in 50 ml of dimethylformamide over a period of 30 minutes while maintaining temperature at 28°–30° C. The pale brown mixture was stirred at room temperature for 6 hours, allowed to stand overnight at room temperature, cooled and treated portionwise with 20 ml of acetic acid (some evolution of gas). The pale yellow slurry was poured onto 2 liters of ice water and extracted with 500 ml of dichloromethane (twice). The organic phases were combined, extracted with 500 ml of water (3 times), dried (magnesium sulfate), filtered and the solvent evaporated to give 99.1 g of a pale brown granular solid. The latter was digested with 150 ml of hot methanol. The suspension was allowed to cool to room temperature, cooled overnight, filtered, washed with cold methanol and dried to give 78.3 g of colorless solid, melting point 117°–119° C., $R_f$ 0.68 (1:1 ethyl acetate-hexane). A sample of material, crystallized from methanol, melted at 117°–119° C.

(B)

[2-(6-Trifluoromethyl-2-aminophenyl)-1-(4-methoxyphenyl)ethyl]propanedioic acid, dimethyl ester Catalytic reduction of 40.4 g (0.088 mol) of [2-(6-trifluoromethyl-2-nitrophenyl)-1-(4-methoxyphenyl)ethyl]propanedioic acid, dimethyl ester (in two portions) following the procedure of Example 28 part B gave 36.9 g of nearly colorless solid, melting point 111°–113° C.

(C)
6-(Trifluoromethyl)-1,3,4,5-tetrahydro-3-(methoxycarbonyl)-4-(4-methoxyphenyl)-2H-1-benzazepin-2-one To a dry 2 liter three-neck flask was added 34.5 g (0.081 mol) of 2-(6-trifluoromethyl-2-aminophenyl)-1-(4-methoxyphenyl)ethyl]propanedioic acid, dimethyl ester and 350 ml of methanol. The suspension was heated to 45° C. and the resulting solution was cooled to 30° C. and treated with 23 ml of 25% solution of sodium methoxide in methanol. This mixture was heated (colorless solid separated at 52° C.) and refluxed for 1 hour. The slurry was cooled to 15° C. and treated with a solution of 30 ml of 6N hydrochloric acid in 350 ml of water. After stirring in an ice bath for 2 hours, the pale gray solid was filtered and dried; yield 30.8 g; melting point 214°–216° C.; $R_f$ 0.33 (1:1 ethyl acetate-hexane). A sample crystallized from methanol melted at 218°–220° C.

(D)
6-(Trifluoromethyl)-1,3,4,5-tetrahydro-3-hydroxy-3-(methoxycarbonyl)-4-(4-methoxyphenyl)-2H-1-benzazepin-2-one A stirred suspension of 6-(trifluoromethyl)-1,3,4,5-tetrahydro-3-(methoxycarbonyl)-4-(4-methoxyphenyl)-2H-1-benzazepin-2-one (10.0 g; 0.025 mol) in 450 ml of tetrahydrofuran (under argon) was cooled to −70° C. and treated in one portion with 20.3 g (0.102 mol) of solid potassium hexamethyldisilazide. Stirring at −70° C. was continued for 1 hour, after which 17.7 ml (0.103 mol) of triethyl phosphite was added and oxygen was passed in while replacing the cooling bath with an ice water bath. After passing in oxygen for a total of 2 hours at 0° C., the reaction was quenched while cold with 29 ml of concentrated hydrochloric acid in 290 ml of water. The cooling bath was removed, the mixture stirred for 0.5 hours, and most of the tetrahydrofuran removed on a rotary evaporator. The residue was shaken with 200 ml of ethyl acetate (3×100 ml). The combined organic layers were washed with N hydrochloric acid (2×70 ml), saturated sodium bicarbonate (70 ml), water (70 ml), saturated sodium chloride (70 ml), dried (magnesium sulfate) and the solvent evaporated to give 20.6 g of an oil. The latter solidified when rubbed under 275 ml of hexane. After cooling overnight, the colorless solid was filtered, washed with hexane, and air dried. Yield, 10.06 g, melting point 175°–177° C. (s. 172° C.). TLC: $R_f$ 0.18 (1:1 ethyl acetate-hexane).

(E)
(cis)-6-(Trifluoromethyl)-1,3,4,5-tetrahydro-3-hydroxy-4-(4-methoxyphenyl]-2H-1-benzazepin-2-one A mixture of 9.0 g (22 mmol) of 6-(trifluoromethyl)-1,3,4,5-tetrahydro-3-hydroxy-3-(methoxycarbonyl)-4-(4-methoxyphenyl)-2H-1-benzazepin-2-one, 170 ml of pyridine, 12.0 g of lithium iodide and 1.5 ml of water was refluxed for 2 hours and the product isolated according to the procedure described in Example 1, Method II, part E to give 7.7 g of a nearly colorless solid. TLC (1:1 ethyl acetate-hexane) indicated a cis/trans ratio of about 5/1. This material was suspended in 70 ml of ether, cooled in the cold room overnight and filtered to give 6.82 g of colorless solid; $R_f$ 0.26 (1:1 ethyl acetate-hexane). To remove the trace of the trans isomer present, the material was crystallized from 90 ml of acetonitrile to give 6.0 g of pure cis product, melting point 212° C.–214° C.

(F)
(cis)-3-(Hydroxy)-1-[2-(dimethylamino)ethyl]-1,3,4,5-tetrahydro-4-(4-methoxyphenyl)-6-(trifluoromethyl)-2H-1-benzazepin-2-one, monohydrochloride To a stirred mixture of 4.5 g (13 mmol) of (cis)-6-(trifluoromethyl)-1,3,4,5-tetrahydro-3-hydroxy-4-(4-methoxyphenyl)-2H-1-benzazepin-2-one and 100 ml of dichloromethane was added 16 ml of water, 8.5 g of barium hydroxide (finely divided), 700 mg of benzyltrimethylammonium chloride and a solution of 6.8 g of 2-dimethylaminoethyl bromide hydrobromide in 8 ml of water. The mixture was stirred rapidly at room temperature for 24 hours. A trace of (cis)-6-(trifluoromethyl)-1,3,4,5-tetrahydro-3-hydroxy-4-(4-methoxyphenyl)-2H-1-benzazepin-2-one was still present at this point. The mixture was diluted with 250 ml of ethyl acetate and 100 ml of water and shaken in a separatory funnel. The layers separated slowly. The aqueous phase was separated and extracted with 50 ml of ethyl acetate (twice). The organic phases were combined, extracted with 50 ml of water and then with 50 ml of brine, dried (magnesium sulfate), filtered and the solvent evaporated to give 5.5 g of a colorless foam-like solid, melting point 113°–116° C. This base was dissolved in 200 ml of ethyl acetate and treated with a solution of 2.6 ml of 5.3N hydrogen chloride (in ethanol) in 25 ml of ethyl acetate. The hydrogen chloride salt separated as a gelatinous material. After standing overnight in the cold, the colorless solid was filtered and washed with ether; yield, 5.80 g; melting point 148°–150° C. (dec.); $R_f$ 0.23 (8:1:1 dichloromethane-methanol-acetic acid).

(G)
(cis)-3-(Acetyloxy)-1-[2-(dimethylamino)ethyl]-1,3,4,5-tetrahydro-4-(4-methoxyphenyl)-6-(trifluoromethyl)-2H-1-benzazepin-2-one, monohydrochloride A suspension of 3.0 g (6.5 mmol) of (cis)-3-(hydroxy)-1-[2-(dimethylamino)ethyl]-1,3,4,5-tetrahydro-4-(4-methoxyphenyl)-6-(trifluoromethyl)-2H-1-benzazepin-2-one, monohydrochloride (finely divided) in 90 ml of acetic anhydride (under nitrogen) was stirred and heated in an oil bath. All of the solid dissolved when the bath temperature reached 90° C. After heating this solution at 113°–115° C. for 5 hours, all of (cis)-3-(hydroxy)-1-[2-(dimethylamino)ethyl]-1,3,4,5-tetrahydro-4-(4-methoxyphenyl)-6-(trifluoromethyl)-2H-1-benzazepin-2-one, monohydrochloride had reacted (TLC). The solvent was removed on a rotary evaporator and the colorless residue (4.6 g) was treated with 25 ml of ethyl acetate and the resulting suspension was diluted with 25 ml of ether, filtered and washed the solid with fresh ether, 2.90 g; melting point 222°–224° C. (dec.)

Analysis Calc'd. for $C_{24}H_{27}N_2F_3O_4 \cdot HCl$: C, 57.54; H, 5.63; N, 5.59; Cl, 7.08; F, 11.39 Found: C, 57.27; H, 5.69; N, 5.43; Cl, 6.92; F, 11.13

EXAMPLE 30

(d-cis)-3-(Acetyloxy)-1-[2-(dimethylamino)ethyl]-1,3,4,5-tetrahydro-4-(4-methoxyphenyl)-6-(trifluoromethyl)-2H-1-benzazepin-2-one, monohydrochloride

(A)
(d,l)-6-(Trifluoromethyl)-1,3,4,5-tetrahydro-4-(4-methoxyphenyl)-2H-1-benzazepin-2-one-3-carboxylic acid To a stirred warm solution of 58.0 g (0.88 mol) of potassium hydroxide (85%) in 500 ml of methanol was added portionwise 81.7 g (0.21 mol) of (d,l)-6-(trifluoromethyl)-1,3,4,5-tetrahydro-3-(methoxycarbonyl)-4-(4-methoxyphenyl)-2H-1-benzazepin-2-one (see Example 29, part C); most of the solid dissolved. The mixture was diluted with 100 ml of dioxane and the resulting solution was refluxed for 6 hours. After standing overnight at room temperature, about 50% of the solvent was removed on a rotary evaporator and the residue was diluted with 4 liters of cold water. The insoluble material was filtered and dried (10 g) and the filtrate was cooled and treated portionwise with 270 ml of acetic acid to give a colorless granular solid. The latter was filtered, washed with cold water and dried in a desiccator, yield 69.0 g, melting point 179°–181° C. (s. 128° C.); $R_f$ 0.43 (18:1:1 dichloromethane-methanol-acetic acid.

(B)
(d)-6-(Trifluoromethyl)-1,3,4,5-tetrahydro-4-(4-methoxyphenyl)-2H-1-benzazepin-2-one-3-carboxylic acid, (S)-α-methylbenzylamine salt A mixture of 67.0 g (0.176 mol) of (d,l)-6-(trifluoromethyl)-1,3,4,5-tetrahydro-4-(4-methoxyphenyl)-2H-1-benzazepin-2-one-3-carboxylic acid and 1 liter of ethanol was warmed and the resulting solution (52° C.) was treated with a solution of 21.4 g (0.176 mol) of (−)-α-methylbenzylamine in 100 ml of ethanol. This solution was seeded and allowed to stand undisturbed for 24 hours at room temperature. The product separated as well-formed crystals on the walls of the flask. The mother liquor was decanted, from the solid and the latter was suspended in 70 ml of ethanol, filtered and washed with fresh ethanol to give 34.6 g of a colorless solid, melting point 156° C. (dec.); $[\alpha]_D + 10.3°$ (c, 1% methanol). $R_f$ 0.40 (18:1:1 dichloromethane-methanol-acetic acid).

(C)
(d)-6-(Trifluoromethyl)-1,3,4,5-tetrahydro-4-(4-methoxyphenyl)-2H-1-benzazepin-2-one-3-carboxylic acid A suspension of 2.50 g (5 mmol) of (d)-6-(trifluoromethyl)-1,3,4,5-tetrahydro-4-(4-methoxyphenyl)-2H-1-benzazepin-2-one-3-carboxylic acid, (S)-α-methylbenzylamine salt in 50 ml of chloroform and 25 ml of water was stirred and treated gradually with 5.5 ml of N hydrochloric acid. The mixture was shaken and treated with 5 ml of methanol to break the emulsion. The organic phase was separated, washed with 25 ml of water, dried over magnesium sulfate, filtered and the solvent removed on a rotary evaporator. Ether was added to the gelatinous residue to give a granular solid and the solvent was removed to give 1.85 g of colorless material, melting point 138° C. (dec.), $[\alpha]_D + 16.6°$ (c, 1% methanol).

(D)
(d)-6-(Trifluoromethyl)-1,3,4,5-tetrahydro-3-(methoxycarbonyl)-4-(4-methoxyphenyl)-2H-1-benzazepin-2-one A stirred suspension of (d)-6-(trifluoromethyl)-1,3,4,5-tetrahydro-4-(4-methoxyphenyl)-2H-1-benzazepin-2-one-3-carboxylic acid, (S)-α-methylbenzylamine salt (6.1 g; 0.0122 mol) in 140 ml of dichloromethane and 70 ml of water was treated with 14 ml of N hydrochloric acid; methanol (35 ml) was added in increments to expedite solution. When two clear layers were obtained, they were separated and the organic phase was washed with 35 ml of water, dried briefly (magnesium sulfate), and filtered. The solution was cooled in an ice bath, stirred gently, and treated with a cold ethereal solution of diazomethane (prepared in 70 ml of ether from 5.2 g of 1-methyl-3-nitro-1-nitrosoguanidine and 19 ml of potassium hydroxide). After stirring in an ice bath for 1 hour (persistent yellow color indicated that excess diazomethane was present), most of the excess diazomethane was destroyed by dropwise addition of acetic acid and the solvents were evaporated. The colorless solid was pump-dried; yield, 4.45 g; melting point 136°–138° C. (s. 133° C.) $[\alpha]_D + 10.6°$ (c, 1% in methanol). TLC: $R_f$ 0.23 (1:1 ethyl acetate-hexane). An additional 6.1 g of (d)-6-(trifluoromethyl)-1,3,4,5-tetrahydro-4-(4-methoxyphenyl)-2H-1-benzazepin-2-one-3-carboxylic acid, (S)-α-methylbenzylamine salt was similarly converted to the methyl ester.

(E)
(d)-6-(Trifluoromethyl)-1,3,4,5-tetrahydro-3-hydroxy-3-(methoxycarbonyl)-4-(4-methoxyphenyl)-2H-1-benzazepin-2-one (d)-6-(Trifluoromethyl)-1,3,4,5-tetrahydro-3-(methoxycarbonyl)-4-(4-methoxyphenyl)-2H-1-benzazepin-2-one (8.38 g; 0.0213 mol) in 420 ml of tetrahydrofuran was treated with 17.5 g (0.0877 mol) of potassium hexamethyldisilazide, then with 15.4 ml (0.0898 mol) of triethyl phosphite, and finally with oxygen for 2 hours as described in Example 1, Method II, part D to give 16.9 g of a yellow oil. The latter was stirred with 175 ml of hexane, cooled overnight, and the hexane liquor decanted. After washing the yellow oil with 70 ml of cold hexane by decantation, the remaining solvent was evaporated, finally at 0.2 mm; yield, 12.85 g. $[\alpha]_D + 123°$ C. (c, 1% in methanol). TLC: $R_f$ 0.18 (1:1 ethyl acetate-hexane).

(F)
(d-cis)-6-(Trifluoromethyl)-1,3,4,5-tetrahydro-3-hydroxy-4-(4-methoxyphenyl)-2H-1-benzazepin-2-one A stirred solution of (d)-6-(trifluoromethyl)-1,3,4,5-tetrahydro-3-hydroxy-3-(methoxycarbonyl)-4-(4-methoxyphenyl)-2H-1-benzazepin-2-one (12.85 g; 0.0213 mol) in 175 ml of pyridine was treated with 11.6 g (0.0867 mol) of lithium iodide and 1.75 ml of water, heated to reflux for 2 hours, and worked up as described in Example 29, part E to give 6.85 g of solid. TLC (1:1 ethyl acetate-hexane) showed a cis/trans ratio of about 5/1. Following trituration with 75 ml of ether and cooling overnight, the colorless solid weighed 5.62 g. To remove a trace of trans isomer, the material was crystallized from 60 ml of acetonitrile and filtered after 4 hours in the cold room; yield, 4.90 g; melting point 220°–222° C. $[\alpha]_D + 116°$ (c, 1% in methanol). $R_f$ 0.19 (1:1 ethyl acetate-hexane).

(G)
(d-cis)-3-(Hydroxy)-1-[2-(dimethylamino)ethyl]-1,3,4,5-tetrahydro-4-(4-methoxyphenyl)-6-(trifluoromethyl)-2H-1-benzazepin-2-one, monohydrochloride A vigorously stirred mixture of (d-cis)-6-(trifluoromethyl)-1,3,4,5-tetrahydro-3-hydroxy-4-(4-methoxyphenyl)-2H-1-benzazepin-2-one (5.17 g; 0.0147 mol) in 115 ml of dichloromethane and 19 ml of water was treated with 9.8 g (0.0311 mol) of pulverized hydrated barium hydroxide, 0.8 g of benzylmethylammonium chloride and 7.9 g (0.0339 mol) of 2-dimethylaminoethyl bromide hydrobromide dissolved in 9.5 ml of water. After stirring for 18 hours, work up as in Example 29, part F gave 6.09 g of colorless solid base; melting point 133°–135° C. (s. 120° C.). $[\alpha]_D+135°$ (c, 1% in methanol).

The base (6.0 g) in 200 ml of methanol was treated with 2.8 ml of 5.35N ethanolic hydrogen chloride and the solvents evaporated to give a sticky foam. The latter was rubbed under 200 ml of ether (solidified), cooled for 2 hours, filtered, and dried in vacuo; yield, 6.65 g; $[\alpha]_D+91.3°$ (c, 1% in methanol). TLC: $R_f$ 0.25 (8:1:1 dichloromethane-methanol-acetic acid).

(H)
(d-cis)-3-(Acetyloxy)-1-[2-(dimethylamino)ethyl]-1,3,4,5-tetrahydro-4-(4-methoxyphenyl)-6-(trifluoromethyl)-2H-1-benzazepin-2-one, monohydro-chloride A stirred solution of (d-cis)-3-(hydroxy)-1-[2-(dimethylamino)ethyl]-1,3,4,5-tetrahydro-4-(4-methoxyphenyl)-6-(trifluoromethyl)-2H-1-benzazepin-2-one, monohydrochloride (6.5 g; 0.0142 mol) in 180 ml of acetic anhydride was heated in an oil bath at 110°–120° C. for 4 hours. TLC (8:1:1 dichloromethane-methanol-acetic acid) showed the reaction to be complete. The bulk of acetic anhydride was removed on a rotary evaporator at 0.2 mm and the syrupy residue (10.6 g) was taken up in 30 ml of ethyl acetate, but on seeding and rubbing, a solid slowly separated. Ether (90 ml) was added in increments (crystallization was now more rapid) and after cooling for 1 hour, the colorless solid was filtered under argon (hygroscopic), washed with ether, and dried in vacuo; yield, 6.2 g; melting point 180°–182° C. (s. 178° C.). $[\alpha]_D+97.1°$ (c, 1% in methanol). TLC:$R_f$ 0.36 (8:1:1 dichloromethane-methanol-acetic acid).

Analysis Calc'd. for $C_{24}H_{27}F_3N_2O_4 \cdot HCl$: C, 57.54; N, 5.63; N, 5.59; F, 11.39; Cl, 7.08 Found: C, 57.35; H, 5.61; N, 5.60; F, 11.11; Cl, 7.18

EXAMPLE 31
(d-cis)-3-(Acetyloxy)-1-2-(dimethylamino)ethyl]-1,3,4,5-tetrahydro-4-(4-methoxyphenyl)-7-(trifluoromethyl)-2H-1-benzazepin-2-one, monohydrochloride

(A)
(cis)-3-(Hydroxy)-1-[2-(dimethylamino)ethyl]-1,3,4,5-tetrahydro-4-(4-methoxyphenyl)-7-(trifluoromethyl)-2H-1-benzazepin-2-one A vigorously stirred suspension of 7.0 g (0.020 mol) of (cis)-7-(trifluoromethyl)-1,3,4,5-tetrahydro-3-hydroxy-4-(4-methoxyphenyl)-2H-1-benzazepin-2-one (see Example 28, part E) in 140 ml of dichloromethane (500 ml recovery flask fitted with magnetic stirrer) was treated with 25 ml of water, followed by 13.3 g (0.042 mol) of pulverized barium hydroxide and 0.8 g of benzyltrimethylammonium chloride. A solution of 10.5 g (0.045 mol) of 2-dimethylaminoethyl bromide hydrobromide in 12 ml of water was then added portionwise. The flask was stoppered and the mixture was vigorously stirred at room temperature and stirring was continued overnight.

Some solids were filtered off, washed with dichloromethane, and the layers in the filtrate separated. The dichloromethane layer was washed with water (2×75 ml), then shaken with 750 ml of water containing 42 ml of N hydrochloric acid. A stubborn emulsion was encountered at this point. Some dichloromethane was drawn off but then the mixture was extracted with 600 ml of ether.

The aqueous phase was layered over with 250 ml of ethyl acetate, basified with 56 ml of N sodium hydroxide, shaken, and separated. The aqueous phase was extracted with ethyl acetate (three times 150 ml), the combined organic layers washed with brine (100 ml), dried (magnesium sulfate), and the solvent evaporated to give a colorless solid which was pump-dried; yield 7.87 g; melting point 136°–138° C. TLC:$R_f$ 0.42 (90:10 dichloromethane-methanol).

(B)
(d-cis)-3-(Hydroxy)-1-[2-(dimethylamino)ethyl]-1,3,4,5-tetrahydro-4-(4-methoxyphenyl)-7-(trifluoromethyl)-2H-1-benzazepin-2-one, (+)-tartaric acid salt (cis)-3-(Hydroxy)-1-[2-(dimethylamino)ethyl]-1,3,4,5-tetrahydro-4-(4-methoxyphenyl)-7-(trifluoromethyl)-2H-1-benzazepin-2-one (15.8 g; 0.0374 mol) and 5.7 g (0.038 mol) of d-(+)-tartaric acid were dissolved in 500 ml of hot methanol, seeded, and the solution allowed to stand undisturbed at room temperature; the tartrate salt separated very slowly. After 3 days, the feathery crystals were filtered, washed with 50 ml of cold methanol, and dried in vacuo; yield, 11.7 g $[\alpha]_D+59.7°$ (c, 1% in acetic acid). This material was taken up in 275 ml of hot methanol, seeded, and kept at room temperature for 2 days to give 5.43 g. $[\alpha]_D+117°$. After recrystallization from 100 ml of hot methanol, the solid weighed 5.02 g; melting point 165°–167° C. $[\alpha]_D+117°$ (c, 1% in acetic acid).

(C)
(d-cis)-3-(Hydroxy)-1-[2-(dimethylamino)ethyl]-1,3,4,5-tetrahydro-4-(4-methoxyphenyl)-7-(trifluoromethyl)-2H-1-benzazepin-2-one (d-cis)-3-(Hydroxy)-1-[2-(dimethylamino)ethyl]-1,3,4,5-tetrahydro-4-(4-methoxyphenyl)-7-(trifluoromethyl)- 2H-1-benzazepin-2-one, (+)-tartaric acid salt was combined with comparable d-(+)-tartrate salt ($[\alpha]_D+117°$) from an earlier experiment (total, 7.17 g), suspended in 200 ml of dichloromethane and 200 ml of water, stirred, treated with 25 ml of N sodium hydroxide, the stirring continued until no solid remained, and the layers separated. The aqueous phase was extracted with dichloromethane (2×100 ml), the combined organic layers washed with water (50 ml), dried (magnesium sulfate), the solvent evaporated, and the residue pump-dried to yield 5.08 g of colorless foamy base. $[\alpha]_D+192°$ (c, 1% in chloroform). The base (5.00 g) in 150 ml of methanol was treated with 2.3 ml of 5.35N ethanolic hydrogen chloride, the solvent removed on a rotary evaporator, and the solid pump-dried; yield 5.57 g. $[\alpha]_D+144°$ (c, 1% in methanol). TLC: $R_f$ 0.24 (8:1:1 dichloromethane-methanol-acetic acid).

(D)

(d-cis)-3-(Acetyloxy)-1-[2-(dimethylamino)ethyl]-1,3,4,5-tetrahydro-4-(4-methoxyphenyl)-7-(trifluoromethyl)-2H-1-benzazepin-2-one, monohydrochloride A stirred solution of (d-cis)-3-(hydroxy)-1-[2-(dimethylamino)ethyl]-1,3,4,5-tetrahydro-4-(4-methoxyphenyl)-7-(trifluoromethyl)-2H-1-benzazepin-2-one (5.55 g; 0.0125 mol) in 150 ml of acetic anhydride was heated in an oil bath at 110°–11B° C. for 4⅝ hours under argon. The bulk of acetic anhydride was removed on a rotary evaporator at 0.2 mm and the colorless solid residue (17 g) was suspended in 75 ml of ethyl acetate, diluted with 150 ml of ether, cooled for 1 hour, filtered, washed with ether, and dried in vacuo; yield 5.6 g; melting point 257°–259° C. (dec.) $[\alpha]_D + 143°$ (c, 1% in methanol). TLC:$R_f$ 0.29 (8:1:1 dichloromethane-methanol-acetic acid).

Analysis Calc'd. for $C_{24}H_{27}F_3N_2O_4 \cdot HCl$: C, 57.54; H, 5.63; N, 5.59; Cl, 7.08; F, 11.39 Found: C, 57.52; H, 5.55; N, 5.57; Cl, 6.90; F, 11.18

EXAMPLE 32

(1-cis)-3-(Acetyloxy)-1-2-(dimethylamino)ethyl]-1,3,4,5-tetrahydro-4-(4-methoxyphenyl)-7-(trifluoromethyl)-2H-1-benzazepin-2-one, monohydrochloride

(A)

(1-cis)-3-(Hydroxy)-1-[2-(dimethylamino)ethyl]-1,3,4,5-tetrahydro-4-(4-methoxyphenyl)-7-trifluoromethyl)-2H-1-benzazepin-2-one, (−)-tartaric acid salt The methanol mother liquor from the initial crystallization of (d-cis)-3-(hydroxy)-1-[2-(dimethylamino)ethyl]-1,3,4,5-tetrahydro-4-(4-methoxyphenyl)-7-(trifluoromethyl)-2H-1-benzazepin-2-one, (+)-tartaric acid salt (see Example 31, part B) was evaporated and the solid pump-dried to give 10.5 g of material. $[\alpha]_D = -34.3°$ (c=1% in acetic acid). The latter was converted to the free base (1N sodium hydroxide; dichloromethane extractions) to give 7.4 g of (1-cis)-3-(hydroxy)-1-2-(dimethylamino)ethyl]-1,3,4,5-tetrahydro-4-(4-methoxyphenyl)-7-(trifluoromethyl)-2H-1-benzazepin-2-one as a brittle foam. $[\alpha]_D = -53.7°$ (c=1% in chloroform). This base and 2.65 g of 1-(−)-tartaric acid were dissolved in 235 ml of hot methanol, seeded and the solution allowed to stand undisturbed at room temperature; the tartrate salt began to separate fairly soon. After standing overnight, the feathery crystals were filtered, washed with 30 ml of cold methanol, and dried in vacuo; yield, 4.57 g. $[\alpha]_D = -115°$ (c=1% in acetic acid). This material was combined with comparable l-tartrate ($[\alpha]_D - 117°$) from an earlier experiment (total 7.8 g) and crystallized from 145 ml of hot methanol to give 6.68 g; melting point 163°–165° C. (s 161° C.); $[\alpha]_D = -118°$ (c=1% in acetic acid).

(B)

(1-cis)-3-(Hydroxy)-1-[2-(dimethylamino)ethyl]-1,3,4,5-tetrahydro-4-(4-methoxyphenyl)-7-(trifluoromethyl)-2H-1-benzazepin-2-one (1-cis)-3-(Hydroxy)-1-[2-(dimethylamino)ethyl]-1,3,4,5-tetrahydro-4-(4-methoxyphenyl)-7-trifluoromethyl)-2H-1-benzazepin-2-one, (−)-tartaric acid sa (6.5 g, 0.0114 mol) was converted to the foamy free base as described in Example 31, part C; yield, 4.69 g $[\alpha]_D = -192°$ (c=1% in chloroform). The latter yielded 5.14 g of the solid hydrochloride salt. $[\alpha]_D = -143°$ (c=1% in methanol). TLC: $R_f = 0.24$ (8:1:1, dichloromethane-methanolacetic acid).

(C)

(1-cis)-3-(Acetyloxy)-1-[2-(dimethylamino)ethyl]-1,3,4,5-tetrahydro-4-(4-methoxyphenyl)-7-(trifluoromethyl)-2H-1-benzazepin-2-one, monohydrochloride A stirred solution of (1-cis)-3-(hydroxy)-1-2-(dimethylamino)ethyl-1,3,4,5-tetrahydro-4-(4-methoxyphenyl)-7-(trifluoromethyl)-2H-1-benzazepin-2-one (5.1 g, 0.011 mol) in 140 ml of acetic anhydride under argon was heated in an oil bath at 111°–119° C. for 4.5 hours. The bulk of the acetic anhydride was removed on the rotary evaporator at 0.2 mm and the solid residue (12.7 g) was suspended in 70 ml of ethyl acetate, diluted with 140 ml of ether, cooled for 1 hour, filtered, washed with ether, and dried in vacuo; yield, 5.08 g; melting point 258°–260° C. (dec.). $[\alpha]_D = -143°$ (c=1% in methanol). TLC: $R_f$ 0.29 (8:1:1, dichloromethane-methanol-acetic acid).

Analysis Calc'd. for $C_{24}H_{27}F_3N_2O_4 \cdot HCl$: C, 57.54; H, 5.63; N, 5.59; Cl, 7.08; F, 11.39 Found: C, 57.63; H, 5.65; N, 5.51; Cl, 6.79; F, 11.26

EXAMPLE 33

(cis)-3-(Acetyloxy)-1-[2-(dimethylamino)ethyl]-7-(2,2-dimethyl-l-oxopropoxy)-1,3,4,5-tetrahydro-4-(4-methoxyphenyl)-2H-1-benzazepin-2-one, monohydrochloride A stirred solution of 0.5 g (1.11 mmol) of (cis)-3-(acetyloxy)-1-[2-(dimethylamino)ethyl]-1,3,4,5-tetrahydro-7-hydroxy-4-(4-methoxyphenyl)-2H-1-benzazepin-2-one, monohydrochloride (see Example 23) in 15 ml of dimethylformamide was treated with 0.095 g (2.38 mmol) of 60% sodium hydride (effervescence), stirred 1 hour at room temperature, added 0.16 ml (1.30 mmol) of pivaloyl chloride, and stirring was continued at room temperature overnight.

After removing the bulk of dimethylformamide on a rotary evaporator at 0.2 mm, the residue was shaken with 20 ml of ethyl acetate and 10 ml of water. The layers were separated, the organic layer washed with water (3×10 ml), saturated sodium chloride (10 ml), dried (magnesium sulfate), and the solvent evaporated. The residue was taken up in ethanol, treated with 0.2 ml of 5.75N ethanolic hydrochloric acid, and the solution evaporated. The residue was rubbed under ether and the evaporation repeated to give a solid. The latter was rubbed under ether, cooled overnight, filtered, and dried in vacuo, yield, 0.37 g. TLC and mass spectrometry showed the material to be a mixture of acetylated and deacetylated products. The material (0.35 g) and 15 ml of acetic anhydride were heated in an oil bath and the resulting solution kept at 105°–110° C. for 4.5 hours. After standing overnight at room temperature, the acetic anhydride was removed on a rotary evaporator to give a solid. The latter was rubbed under ethyl acetate, treated with some ethanolic hydrogen chloride to pH 2, evaporated, rubbed under ether, the evaporation repeated, and the solid kept under fresh ether in the cold overnight. The colorless product was filtered, washed with ether, and dried in vacuo; yield, 0.37 g; melting point 198°–200° C. (dec.); s. 160° C. TLC: $R_f = 0.40$ (90:10 dichloromethane-methanol).

Analysis Calc'd. for $C_{28}H_{36}N_2O_6 \cdot HCl \cdot 1.5H_2O$: C, 60.04; H, 7.20; N, 5.00; Cl, 6.33 Found: C, 60.30; H, 7.00; N, 4.86; Cl, 6.06

EXAMPLE 34

(cis)-3-(Acetyloxy)-1-[2-(dimethylamino)ethyl]-1,3,4,5-tetrahydro-4-(4-methoxyphenyl)-2-oxo-1H-1-benzazepin-7-ol, dimethylcarbamate ester, monohydrochloride A stirred solution of 0.75 (1.67 mmol) of (cis)-3-(acetyloxy)-1-2-(dimethylamino)ethyl]-1,3,4,5-tetrahydro-7-hydroxy-4-(4-methoxyphenyl)-2H-1-benzazepin-2-one, monohydrochloride (see Example 23) in 25 ml of dimethylformamide was treated with 0.14 g (3.5 mmol) of 60% sodium hydride and stirred for 1 hour at room temperature. Dimethylcarbamyl chloride (0.20 ml, 2.17 mmol) was then added and stirring was continued at room temperature. After stirring overnight, some starting material was still present. An additional 0.05 ml of halide was added and since after 3 hours some starting material continued to be present, the dimethylformamide was removed on a rotary evaporator at 0.2 mm and the residue was shaken with 30 ml of ethyl acetate and 15 ml of water. The layers were separated and the aqueous phase was extracted with 15 ml of ethyl acetate. The combined organic layers were washed with water (2×15 ml), brine (10 ml), dried (magnesium sulfate), and the solvent evaporated to give 0.8 g of a very viscous residue. Since TLC showed two spots of about equal intensity, the material was redissolved in ethyl acetate, washed with water containing 1N sodium hydroxide, then with water and brine, dried and evaporated. TLC of the amorphous solid (0.66 g) still showed two spots. Mass spectrum indicated a mixture of acetylated and deacetylated products.

The above mixture was heated in 30 ml of acetic anhydride at 105°–110° C. (bath temperature) for 4 hours and kept overnight at room temperature. The acetic anhydride was removed at 0.2 mm to give a glass-like residue which was rubbed under ether and evaporated. The amorphous solid was triturated with ether, cooled overnight, and filtered; yield, 0.65 g. This material (0.62 g) when stirred in 5 ml of warm ethyl acetate almost all dissolved, then a solid rapidly separated. When crystallization appeared to be almost complete, ether was added to 25 ml and after cooling overnight the colorless solid was filtered, washed with ether, and dried in vacuo; yield, 0.53 g; melting point 178°–181° C. (bubbles); s, 168° C. TLC: $R_f$=0.19 (8:1:1, chloroform-methanol-acetic acid).

Analysis Calc'd. for $C_{26}H_{33}N_3O_6.HCl.0.75H_2O$: C, 58.53; H, 6.70; N, 7.58; Cl, 6.65 Found: C, 58.58; H, 6.40; N, 7.44; Cl, 6.79

EXAMPLE 35

(cis)-3-(Acetyloxy)-1-[2-(dimethylamino)ethyl]-1,3,4,5-tetrahydro-7-[[(methylamino)carbonyl]-oxy]-4-(4-methoxyphenyl)-2H-1-benzazepin-2-one, monohydrochloride A stirred suspension of 0.5 g of (cis)-3-(acetyloxy)-1-[2-(dimethylamino)ethyl]-1,3,4,5-tetrahydro-7-hydroxy-4-(4-methoxyphenyl)-2H-1-benzazepin-2-one, monohydrochloride (see Example 23) in 10 ml of acetonitrile was treated with 0.65 ml (4.66 mmol) of methyl isocyanate, and stirred at room temperature. After standing overnight, volatiles were removed on a rotary evaporator and the residue was shaken with 20 ml of ethyl acetate and 5 ml of water containing 2 ml of 10% sodium bicarbonate. Most of the color entered the aqueous phase. The layers were separated and the aqueous phase was extracted with ethyl acetate (3×5 ml). The combined organic layers were washed with 5 ml of saturated sodium chloride solution, dried (magnesium sulfate), and the solvent evaporated to give 0.72 g of oil. The latter was taken up in 5 ml of ethyl acetate and treated with 0.2 ml of 5.75N ethanolic hydrogen chloride. The hydrogen chloride salt separated as a gum which crystallized on seeding and rubbing. The solvents were evaporated, the solid rubbed under ether, evaporated, and finally pump-dried. The nearly colorless solid was rubbed under ether, cooled overnight, filtered, washed with ether, and dried in vacuo; yield, 0.51 g; melting point 216°–218° C. (dec.); s, 212° C. TLC: $R_f$=0.24 (90:10 dichloromethane-methanol).

Analysis Calc'd. for $C_{25}H_{31}N_3O_6.HCl.H_2O$: C, 57.30; H, 6.38; N, 8.02; Cl, 6.77 Found: C, 57.08; H, 6.28; N, 8.34; Cl, 6.84

EXAMPLE 36

(cis)-3-(Acetyloxy)-1-[2-(1-pyrrolidinyl)ethyl]-1,3,4,5-tetrahydro-4-(4-methoxyphenyl)-7-(trifluoromethyl)-2H-1-benzazepin-2-one, monohydrochloride (A)

(cis)-3-Hydroxy-1-2-(1-pyrrolidinyl)ethyl]-1,3,4,5-tetrahydro-4-(4-methoxyphenyl)-7-(trifluoromethyl)-2H-1-benzazepin-2-one, monohydrochloride A vigorously stirred suspension of 1.98 g (5.6 mmol) of (cis)-3-hydroxy-7-(trifluoromethyl)-1,3,4,5-tetrahydro-4-(4-methoxyphenyl)-2H-1-benzazepin-2-one in 40 ml of dichloromethane (100 ml recovery flask fitted with magnetic stirrer) was treated with 7 ml of water, followed by 3.8 g (12.0 mmol) of pulverized barium hydroxide and 0.2 g of benzyltrimethylammonium chloride. A solution of 3.4 g (13.1 mmol) of N-(2-bromoethyl)pyrrolidine hydrobromide in 3.5 ml of water was then added portionwise. The flask was stoppered and the mixture was vigorously stirred at room temperature overnight.

Ethyl acetate (120 ml) and water (20 ml) were added, the mixture was shaken, and the layers separated. The milky aqueous phase was back-extracted with 20 ml of ethyl acetate. The combined organic layers were washed with water (3×20 ml), brine (20 ml), dried (magnesium sulfate), and the solvents evaporated. After pump-drying, the colorless solid weighed 2.58 g; melting point 134°–136° C. (s, 131° C.). TLC: $R_f$=0.46 (90:10, chloroform-methanol).

Analysis Calc'd. for $C_{24}H_{27}F_3N_2O_3$: C, 64.27; H, 6.07; N, 6.25; F, 12.71 Found: C, 64.02; H, 6.18; N, 6.05; F, 12.51

The above base (2.5 g) in 50 ml of chloroform was treated in 1.2 ml of 5.35N ethanolic hydrogen chloride, the solvent evaporated, and the amorphous solid pump-dried; yield, 3.3 g.

(B)

(cis)-3-(Acetyloxy)-1-[2-(1-pyrrolidinyl)ethyl]-1,3,4,5-tetrahydro-4-(4-methoxyphenyl)-7-(trifluoromethyl)-2H-1-benzazepin-2-one, monohydrochloride A stirred solution of (cis)-3-hydroxy-1-[2-(1-pyrrolidinyl)ethyl]-1,3,4,5-tetrahydro-4-(4-methoxyphenyl)-7-(trifluoromethyl)-2H-1-benzazepin-2-one, monohydrochloride (3.3 g, 0.0056 mmol) in 80 ml of acetic anhydride under argon was heated in an oil bath at 114°–119° C. for 4.5 hours. The bulk of acetic anhydride was removed on a rotary evaporator at 0.2 mm and the solid residue (12 g) was suspended in 30 ml of ethyl acetate, diluted with 60 ml of ether, cooled for 1 hour, filtered, washed with ether, and dried in vacuo overnight; yield, 2.60 g; melting point 228°–230° C. (dec.); s, 225° C. TLC: R$_f$ =0.48 (8:1:1, chloroform-methanol-acetic acid).

Analysis Calc'd. for C$_{26}$H$_{29}$F$_3$N$_2$O$_4$.HCl.H$_2$O: C, 57.30; H, 5.92; N, 5.14; Cl, 6.51; F, 10.46 Found: C, 57.43; H, 5.70; N, 4.99; Cl, 6.29; F, 10.22

EXAMPLE 37

(cis)-3-(Acetyloxy)-7-chloro-1-[3-(dimethylamino)-propyl]-1,3,4,5-tetrahydro-4-(4-methoxyphenyl)-2H-1-benzazepin-2-one, monohydrochloride (A)

(cis)-3-(Hydroxy)-7-chloro-1-[3-(dimethylamino)-propyl]-1,3,4,5-tetrahydro-4-(4-methoxyphenyl)-2H-1-benzazepin-2-one, monohydrochloride One gram (3.15 mmol) of (cis)-3-(hydroxy)-7-chloro-1,3,4,5-tetrahydro-4-(4-methoxyphenyl)-2H-1-benzazepin-2-one was treated with 0.135 g (3.38 mmol) of 60% sodium hydride in 30 ml of dimethylformamide, then with 2.2 ml (4.73 mmol) of 2.15N 3-dimethylaminopropyl chloride in toluene and heated for 3 hours at 75°–83° C. The reaction was then diluted with water and extracted with ether. The aqueous phase was reextracted with ether, and the combined organic layers dried (magnesium sulfate), and the solvent evaporated, finally at 0.2 mm, to give 0.85 g of base as a sticky foam. the latter, in 30 ml of ethanol, was treated with 0.43 ml of 5.75N ethanolic hydrogen chloride and the solvent evaporated. The solid residue was rubbed under ether and the evaporation repeated. After pump-drying, the colorless solid weighed 0.97 g; melting point 67°–69° C. (on continued heating, sample solidified and remelted at 191°–193° C.). TLC: R$_f$=0.26 (8:1:1, dichloromethane-methanol-acetic acid).

(B)

(cis)-3-(Acetyloxy)-7-chloro-1-[3-(dimethylamino)-propyl]-1,3,4,5-tetrahydro-4-(4-methoxyphenyl)-2H-1-benzazepin-2-one, monohydrochloride A stirred suspension of (cis)-3-(hydroxy)-7-chloro-1-[3-(dimethylamino)propyl]-1,3,4,5-tetrahydro-4-(4-methoxyphenyl)-2H-1-benzazepin-2-one, monohydrochloride (0.96 g; 2.18 mmol) in 35 ml of acetic anhydride was heated in an oil bath under argon and the resulting solution kept at 115°–118,° C. for 3 hours. The acetic anhydride was removed on a rotary evaporator at 0.2 mm to give a solid. The latter was rubbed under ethyl acetate, treated with 0.5 ml of saturated hydrogen chloride in ether to pH 2 and the evaporation repeated. The solid was rubbed under ether, evaporated, and pump-dried. The colorless material was rubbed under fresh ether, cooled overnight, filtered, washed with ether, and dried in vacuo; yield, 0.96 g; melting point 212°–215° C. (dec.), s, 200° C. TLC: R$_f$=0.32 (8:1:1, dichloromethane-methanol-acetic acid).

Analysis Calc'd. for C$_{24}$H$_{29}$ClN$_2$O$_4$.0.25H$_2$O: C, 59.32; H, 6.33; N, 5.77; Cl, 14.59 Found: C, 59.30; H, 6.25; N, 5.67; Cl, 14.89

EXAMPLE 38

(cis)-3-Methoxy-1-[2-(dimethylamino)ethyl]-1,3,4,5-tetrahydro-4-(4-methoxyphenyl)-7-(trifluoromethyl)-2H-1-benzazepin-2-one, monohydrochloride (A)

(cis)-3-(Hydroxy)-1-[2-(dimethylamino)ethyl]-1,3,4,5-tetrahydro-4-(4-methoxyphenyl)-7-(trifluormethyl)-2H-1-benzazepin-2-one, monohydrochloride A suspension of 7-(trifluoromethyl)-1,3,4,5-tetrahydro-3-hydroxy-4-(4-methoxyphenyl)-2H-1-benzazepin-2-one (1.0 g, 2.85 mmol; see Example 28E) in 20 ml of dichloromethane was treated with 3.6 ml of water followed by the addition of barium hydroxide octahydrate (1.89 g, 5.99 mmol) and benzyl trimethylammonium chloride (0.12 g, 0.63 mmol). A solution of 2-dimethylaminoethyl bromide, hydrobromide in 2 ml of water was added portionwise with a pipette. Vigorous stirring under argon was carried out for 72 hours. An additional 0.33 g of 2-dimethylaminoethyl bromide, hydrobromide was added and stirring was continued overnight. The reaction mixture was filtered. The dichloromethane layer was washed twice with water. Hydrochloric acid (1M) was added, the dichloromethane was removed in vacuo, the aqueous layer was washed three times with ethyl acetate, made basic with 1M sodium hydroxide solution, and washed three times with ethyl acetate. The ethyl acetate layers were dried over sodium sulfate and evaporated in vacuo to yield 0.52 g of a white solid. Evaporation in vacuo of the ethyl acetate layers from the 1M hydrochloric acid washes yielded 0.52 g of a tan solid which was dissolved in chloroform, treated with saturated hydrogen chloride-ether solution and triturated with ether.

Filtration yielded an off-white solid which was dissolved in ethyl acetate, washed three times with saturated potassium bicarbonate solution, dried (sodium sulfate), evaporated in vacuo and combined with the 0.52 g of product from above. Total yield: 0.82 g of an off-white solid.

(B)

(cis)-3-Methoxy-1-[2-(dimethylamino)ethyl]-1,3,4,5-tetrahydro-4-(4-methoxyphenyl)-7-(trifluoromethyl)-2H-1-benzazepin-2-one, monohydrochloride A solution of (cis)-3-(hydroxy)-1-[2-(dimethylamino)ethyl]-1,3,4,5-tetrahydro-4-(4-methoxyphenyl)-7-(trifluoromethyl)-2H-1-benzazepin-2-one, monohydrochloride (0.81 g, 1.92 mmol) in 21 ml of dimethylformamide was treated with sodium hydride (0.23 g, 5.76 mmol of a 60% mineral oil dispersion) at room temperature under argon. Stirring was continued for 30 minutes. The temperature was lowered to 0° C., iodomethane was added (0.13 ml, 2.11 mmol) and the reaction was continued for 1½ hours at 0° C. The reaction was quenched at 0° C. with water. Dimethylformamide and water were removed in vacuo. Hexane and 1M hydrochloric acid were added, the aqueous layer was washed twice with hexane, made basic with saturated aqueous potassium carbonate solution and washed three times with ethyl acetate. The ethyl acetate layers were washed with brine, dried over sodium sulfate, and evaporated in vacuo to yield 0.95 g of an oil. This material was dissolved in a minimal amount of chloroform, treated with saturated hydrogen chloride-ether solution, evaporated in vacuo and triturated with ether- /ethyl acetate/methanol (80:15:5) to yield 0.67 g of a white solid, melting point 148° C. (dec).

EXAMPLE 39

(cis)-3-(Acetyloxy)-1-[2-(dimethylamino)ethyl]-1,3,4,5-tetrahydro-4-(4-methoxyphenyl)-6-nitro-2H-1-benzazepin-2-one, monohydrochloride

(A) 2-(Benzylidineamino)-6-nitrotoluene

A mixture of 7.6 g (0.050 mol) of 2-methyl-3-nitro aniline, 12.0 g (0.056 mol) of benzaldehyde and 60 ml of xylene was heated to reflux. Water was rapidly formed and collected in a Dean-Stark tube. Evolution of water ceased after 90 minutes and the solvent was removed on a rotary evaporator at 0.2 mm. The oily residue (12.6 g) was digested with 50 ml of hot hexane and cooled overnight at room temperature. The resulting solid was filtered to give 11.0 g of a pale yellow material, melting point 51°–52° C. The analytical sample was purified by chromatography of a chloroform solution on silica gel to give a pale yellow material, melting point 52°–54° C., $R_f$ 0.43 and 0.50 syn and anti-isomers (chloroform).

(B) [2-(2-Benzylidineamino-6-nitrophenyl)-1-(4-methoxyphenyl)ethyl]propanedioic acid, dimethyl ester To a dry 500 ml three-neck flask equipped with a stirrer, thermometer, condenser and dropping funnel was added 10.0 g (0.04 mol) of dimethyl(4-methoxybenzylidene)malonate and 75 ml of dimethylformamide. This solution was stirred (under nitrogen), treated with 2.0 g (0.05 mol) of 60% sodium hydride dispersion and to this slurry was added dropwise a solution of 9.6 g (0.04 mol) of 2-(benzylidineamino)-6-nitrotoluene in 10 ml of dimethylformamide over a period of 20 minutes while maintaining the temperature at 28°–30° C. After 1 hour, the mixture was heated at 40°–45° C. for 1 hour causing a pale brown color. After heating at 55°–60° C. for 1 hour, the brown solution was allowed to stand overnight at room temperature. The mixture was then processed as described under Example 29, part A to give 18.6 g of dark brown gummy residue. Part of this material (7.87 g) was purified by chromatography on 210 g of silica gel eluting with dichloromethane to give 5.80 g of product as a pale red syrupy residue; $R_f$ 0.18 and 0.26, syn and anti-isomers (dichloromethane). Several other minor components were also present.

(C) [2-(2-Amino-6-nitrophenyl)-1-(4-methoxyphenyl)ethyl]propanedioic acid, dimethyl ester A stirred solution of [2-(2-benzylidineamino-6-nitrophenyl)-1-(4-methoxyphenyl)ethyl]-propanedioic acid, dimethyl ester (9.6 g; approximately 0.02 mol) in 600 ml of methanol (warmed slightly to dissolve) was cooled to 24° C., added 60 ml of water, treated with 3 ml (0.054 mol) of concentrated sulfuric acid, and stirred at room temperature. After 3.5 hours, the reaction appeared to be complete by TLC (1:1 ethyl acetatehexane). Most of the methanol was removed on a rotary evaporator and the residue was stirred with 400 ml of dichloromethane and 100 ml of water while adding portionwise 10 g of sodium bicarbonate in 120 ml of water to basify the aqueous phase. The layers were separated and the aqueous phase was extracted with dichloromethane (2×100 ml). The combined organic layers were washed with 100 ml of water, dried (magnesium sulfate) and evaporated. The residue was rubbed under 200 ml of hexane and cooled overnight. The hexane liquor was decanted, the residue washed with some fresh hexane by decantation and pump-dried to give 8.67 g of a red-orange, sticky product.

(D) 6-Nitro-1,3,4,5-tetrahydro-3-(methoxycarbonyl)-4-(4-methoxyphenyl)-2H-1-benzazepin-2-one A stirred suspension of [2-(2-amino-6-nitrophenyl)-1-(4-methoxyphenyl)ethyl]propanedioic acid, dimethyl ester (9.17 g; 0.021 mol) in 100 ml of methanol (almost all dissolved) was treated with 6.0 ml of 25% sodium methoxide in methanol and heated to reflux (deep red color). After 1.5 hours of heating, the mixture was cooled, stirred and treated with 100 ml of water containing 8.0 ml of 6N hydrochloric acid, followed by 100 ml of water, to precipitate a gum which solidified on rubbing and stirring in an ice bath. After 2 hours, the yellow solid was filtered, washed with water and air dried, then in vacuo overnight; yield, 7.6 g. The latter was stirred with 120 ml of hot methanol, allowed to cool to room temperature, then cooled overnight to give 4.77 g of a light yellow solid; melting point 213°–215° C. (dec.). TLC: R 0.15 (1:1 ethyl acetate-hexane); $R_f$ 0.49 (95:5 dichloromethane-methanol)

(E) 6-Nitro-1,3,4,5-tetrahydro-3-hydroxy-3-(methoxycarbonyl)-4-(4-methoxyphenyl)-2H-1-benzazepin--b 2-one 6-Nitro-1,3,4,5-tetrahydro-3-(methoxycarbonyl)-4-(4-methoxyphenyl)-2H-1-benzazepin-2-one (5.05 0.014 mol) in 250 ml of tetrahydrofuran was treated with 10.9 g (0.055 mol) of potassium hexamethyldisilazide at −70° C., then with 9.6 ml (0.056 mol) of triethyl phosphite and oxygen gas at −70 to 0° C. as described in Example 1, Method II, part D. The solution became very dark on adding the base and did not lighten on passing in oxygen. Workup according to the reference procedure gave 8.7 g of a deep red oil which did not crystallize following trituration with hexane. The final yield of a deep red oil was 5.3 g.

(F) (cis)-3-Hydroxy-1,3,4,5-tetrahydro-6-nitro-4-(4-methoxyphenyl)-2H-1-benzazepin-2-one A mixture of crude 6-nitro-1,3,4,5-tetrahydro-3-hydroxy-3-(methoxycarbonyl)-4-(4-methoxyphenyl)-2H-1-benzazepin-2-one (5.3 g) 120 ml of pyridine, 7.4 g of lithium iodide and 1.2 ml of water was refluxed for 2 hours and worked up according to the procedure of Example 1, Method II, part E to give 4.0 g of brown semi-solid. Trituration with 50 ml of ether and cooling gave 2.05 g of a tan solid. When the latter was taken up in 10 ml of hot acetonitrile and allowed to cool, finally at 5° C., a finely divided solid separated very slowly. After 3 days in the cold, the pale yellow solid was filtered, washed with some cold acetonitrile and air dried; yield, 0.75 g; melting point 198°–200° C. (s. 195° C.).

(G) (cis)-3-(Hydroxy)-1-[2-(dimethylamino)ethyl-1,3,4,5-tetrahydro-4-(4-methoxyphenyl)-6-nitro-2H-1-benzazepin-2-one, monohydrochloride A vigorously stirred mixture of (cis)-3-hydroxy-1,3,4,5-tetrahydro-6-nitro-4-(4-methoxyphenyl)-2H-1-benzazepin-2-one (0.72 g; 2.19 mmol), 20 ml of dichloromethane and 2.7 ml of water was treated with 1.45 g (4.6 mmol) of hydrated barium hydroxide, 0.1 g of benzyltrimethylammonium chloride and 1.15 g (4.9 mmol) of 2-dimethylamino ethyl bromide hydrobromide in 1.3 ml of water as described in Example 29, part F. The reaction was worked up after 3.5 hours to give 0.80 g of a pale yellow solid; melting point 142°–144° C. (s. 140° C.). The above base (0.77 g) in chloroform yielded 0.98 g of the hydrochloride salt as a pale yellow amorphous solid (solvent present).

(H)

(cis)-3-(Acetyloxy)-1-[2-(dimethylamino)ethyl]-1,3,4,5-tetrahydro-4-(4-methoxyphenyl)-6-nitro-2H-1-benzazepin-2-one, monohydrochloride A stirred suspension of the hydrochloride salt of (cis)-3-(hydroxy)-1-[2-(dimethylamino)ethyl]-1,3,4,5-tetrahydro-4-(4-methoxyphenyl)-6-nitro-2H-1-benzazepin-2-one, monohydrochloride (approximately 1.93 mmol) in 30 ml of acetic anhydride was heated to 100° C. (oil bath) and the resulting solution heated at 110°–120° C. for 4.5 hours. After removing the bulk of acetic anhydride on a rotary evaporator at 0.2 mm, the solid residue (2 g) was rubbed under 10 ml of ethyl acetate and diluted portionwise with 20 ml of ether. After cooling overnight, the colorless solid was filtered under argon, washed with ether and dried in vacuo; yield, 0.84 g; melting point 198°–200° C. (dec.), s. 192° C.

Analysis Calc'd. for $C_{23}H_{27}N_3O_6 \cdot HCl \cdot H_2O$: C, 55.70; H, 6.09; N, 8.28; Cl, 7.15 Found: C, 55.54; H, 5.75; N, 8.15; Cl, 6.89

EXAMPLE 40

(d-cis)-6-(Trifluoromethyl)-1,3,4,5-tetrahydro-3-hydroxy-4-(4-methoxyphenyl)-1-[2-[(methyl)(phenylmethyl)amino]ethyl]-2H-1-benzazepin-2-one, monohydrochloride A vigorously stirred mixture of (d-cis)-6-(trifluoromethyl)-1,3,4,5-tetrahydro-3-hydroxy-4-(4-methoxyphenyl)-2H-1-benzazepin-2-one (6.0 g; 0.0171 mol; see Example 30, part F), 240 ml of dichloromethane and 24 ml of water was treated with 8.7 g (0.0276 mol) of pulverized hydrated barium hydroxide, 2.4 g of benzyltrimethylammonium chloride and 8.4 g (0.0272 mol) of N-benzyl-N-methylaminoethyl bromide hydrobromide. After stirring overnight, the mixture was worked up as in Example 29, part F to give 11.3 g of a viscous oil. After standing overnight to allow excess basic bromide to quaternize, the material was shaken with 600 ml of ether containing 90 ml of ethyl acetate and 300 ml of water and the layers separated. The aqueous phase was extracted with 300 ml of ether containing 45 ml of ethyl acetate and the combined organic layers were washed with 150 ml of water, 90 ml of brine, dried (magnesium sulfate), and evaporated. After pump-drying, the very viscous product weighed 8.2 g.

The base in 300 ml of methanol was treated with 3.5 ml of 5N ethanolic hydrogen chloride and the solvent evaporated. The residue was rubbed under ether and the evaporation repeated. After pump-drying, the colorless hydrochloride salt weighed 8.74 g; melting point 99°–102° C. (foaming); s. 85° C.; $[\alpha]_D + 75°$ (c, 1% in methanol).

EXAMPLE 41

(d-cis)-1,3,4,5-Tetrahydro-3-hydroxy-4-(4-methoxyphenyl)-1-2-(methylamino)ethyl]-6-(trifluoromethyl)-2H-1-benzazepin-2-one, monohydrochloride A solution of (d-cis)-6-trifluoromethyl)-1,3,4,5-tetrahydro-3-hydroxy-4-(4-methoxyphenyl)-1-[2-[(methyl)(phenylmethyl)amino]ethyl]-2H-1-benzazepin-2-one, monohydrochloride (4.6 g; 0.0086 mol; see Example 40) in 140 ml of acetic acid was treated with 3.5 g of 10% palladium on charcoal and shaken on the Parr hydrogenator at 50 pounds pressure for 4 hours. The catalyst was filtered off under argon, washed with acetic acid and the acetic acid removed on a rotary evaporator at 0.2 mm (last traces azeotroped with toluene) to give a solid. The latter was rubbed under ether, the evaporation repeated, and the nearly colorless solid pump-dried; wt., 3.74 g; melting point 220° C. (dec.); s. 218° C. Following crystallization (of 3.6 g) from 35 ml of hot methanol-70 ml of ether, the colorless material weighed 2.92 g; melting point 224°–226° C. (dec.); $[\alpha]_D + 89°$ (c, 1% in methanol).

Analysis Calc'd. for $C_{21}H_{23}F_3N_2O_3 \cdot HCl \cdot 0.5H_2O$: C, 55.57; H, 5.55; N, 6.17; Cl, 7.81; F, 12.81 Found: C, 55.52; H, 5.71; N, 6.15; Cl, 8.01; F, 13.08

EXAMPLE 42

(d-cis)-3-(Acetyloxy)-1,3,4,5-tetrahydro-4-(4-methoxyphenyl)-1-[2-[(methyl)(phenylmethyl)amino]-ethyl]-2H-1-benzazepin-2-one, monohydrochloride A stirred solution of 1.9 g (0.0036 mole) of (d-cis)-6-(trifluoromethyl)-1,3,4,5-tetrahydro-3-hydroxy-4-(4-methoxyphenyl)-1-[2-[(methyl)(phenylmethyl)amino]ethyl]-2H-1-benzazepin-2-one, monohydrochloride (see Example 40) in 50 ml of acetic anhydride was heated at 111°–120° C. (oil bath temperature) for 4.25 hours. The bulk of acetic anhydride was removed on a rotary evaporator at 0.2 mm to give 3.5 g of an oily residue. The latter slowly solidified when rubbed under 100 ml of ether and cooled overnight. The ether liquor was decanted and the material washed with cold ether by decantation. After pump-drying, the colorless solid weighed 1.35 g; melting point 66°–68° C. (foaming).

EXAMPLE 43

(d-cis)-3-(Acetyloxy)-1,3,4,5-tetrahydro-4-(4-methoxyphenyl)-1-[2-(methylamino)ethyl]-6-(trifluoromethyl)-2H-1-benzazepin-2-one, monohydrochloride A solution of (d-cis)-3-(acetyloxy)-1,3,4,5-tetrahydro-4-(4-methoxyphenyl)-1-2-[(methyl)-(phenylmethyl)amino]ethyl]-2H-1-benzazepin-2-one, monohydrochloride (1.0 g; 0.00173 mol; see Example 42) in 50 ml of acetic acid was treated with 0.75 g of 10% palladium on charcoal and shaken on the Parr hydrogenator at 50 pounds pressure for 3.5 hours. The catalyst was filtered off under argon, washed well with acetic acid, and the acetic acid removed on a rotary evaporator at 0.2 mm (remaining acetic acid azeotroped with toluene). The syrupy residue was rubbed under ether and the evaporation repeated to give a partly solid gum. The latter was taken up in ethyl acetate, treated with about 1 ml of saturated ethereal hydrogen chloride to pH 2, and the solvent evaporated to give a brittle residue. The latter slowly formed a solid when rubbed under ether. After storing the mixture in the cold room for 3 days, the resulting colorless solid was filtered under argon, washed with ether, and dried in vacuo; wt. 0.55 g; melting point 83°–86° C. (foaming); s. 68° C.; $[\alpha]_D +81°$ (c, 1% in methanol).

Analysis Calc'd. for $C_{23}H_{25}F_3N_2O_4 \cdot HCl \cdot 1.5H_2O$: C, 53.75; H, 5.69; N, 5.45; Cl, 6.90 Found: C, 53.44; H, 5.43; N, 5.55; Cl, 7.10

EXAMPLE 44

(d-cis)-1,3,4,5-Tetrahydro-3-hydroxy-4-(4-hydroxyphenyl)-1-2-(methylamino)ethyl]-6-(trifluoromethyl)-2H-1-benzazepin-2-one, monohydrochloride A stirred suspension (almost all dissolved) of 0.5 g (1.12 mmol) of (d-cis)-1,3,4,5-tetrahydro-3-hydroxy-4-(4-methoxyphenyl)-1-[2-(methylamino) ethyl]-6-(trifluoromethyl)-2H-1-benzazepin-2-one, monohydrochloride (see Example 41) in 25 ml of chloroform was cooled in ice water and treated via syringe with 6 ml (6.0 mmol) of 1M boron tribromide in dichloromethane; a solid separated. The cooling bath was removed and stirring was continued, finally overnight.

The mixture was cooled and treated portionwise with a solution of 2 g of sodium bicarbonate in 40 ml of water. An additional 0.5 g of sodium bicarbonate and 10 ml of water was needed to bring the pH to approximately 8. After stirring for 0.5 hours, 25 ml of chloroform was added and the layers separated. The aqueous phase was extracted with chloroform (2×25 ml), the combined organic layers dried (magnesium sulfate), and the solvent evaporated, finally at 0.2 mm to give 0.39 g of amorphous product.

The base in 30 ml of methanol was treated with 0.21 ml of 5N ethanolic hydrogen chloride and the solvents evaporated. The residue was rubbed under ether and the evaporation repeated. Following pump-drying, the cream colored solid weighed 0.39 g. This was combined with 0.35 g of material from a similar subsequent experiment, triturated with 20 ml of hot ethyl acetate, allowed to cool to room temperature, diluted portionwise with 50 ml of ether, and cooled overnight to give 0.61 g of nearly colorless solid; melting point 150°–153° C. (bubbles); s. 135° C. $[\alpha] +85°$ (c, 1% in methanol).

Analysis Calc'd. for $C_{20}H_{21}F_3N_2O_3 \cdot HCl \cdot 0.5H_2O$: C, 54.61; H, 5.27; N, 6.37; Cl, 8.06 Found: C, 54.86; H, 5.17; N, 6.13; Cl, 8.11

EXAMPLE 45

(d-cis)-1-(2-Dibenzylaminoethyl)-1,3,4,5-tetrahydro-3-hydroxy-4-(4-methoxyphenyl)-6-trifluoromethyl-2H-1-benzazepin-2-one, hydrochloride A vigorously stirred mixture of (d-cis)-1,3,4,5-tetrahydro-3-hydroxy-4-(4-methoxyphenyl)-6-trifluoromethyl-2H-1-benzazepin-2-one (3.0 g, 0.0085 mol, see Example 30, Part F), 100 ml of dichloromethane and 15 ml of water was treated with 4.5 g (0.014 mol) of pulverized hydrated barium hydroxide, 5.25 g (0.014 mol) of dibenzylaminoethyl bromide hydrobromide and 1.3 g of benzyltrimethylammonium chloride (phase-transfer catalyst). N-Alkylation was rapid and almost complete in two hours. After seven hours, the stirrer was stopped and the mixture was allowed to stand overnight at room temperature. The organic solvent was removed on a rotary evaporator and the residue was then treated with 200 ml of ethyl acetate and 50 ml of water. The mixture was shaken and the aqueous phase was discarded. The organic phase was then extracted with (1) 50 ml of water, (2) a solution of 5 ml of 1N hydrochloric acid in 50 ml of water, and (3) 50 ml of water. After drying over magnesium sulfate, the solvent was evaporated to give 6.6 g of residue. This material was dissolved in 40 ml of methanol and treated with a solution of 1.8 ml of 5.1N hydrogen chloride in ethanol. The slightly acidic solution was concentrated on a rotary evaporator to give a semi-solid residue. Trituration of this material with 50 ml of ether gave a granular solid. The solvent was removed on a rotary evaporator and the resulting solid was suspended in 70 ml of ether and allowed to stand at room temperature overnight. The solvent was decanted from the solid and the latter triturated with 50 ml of fresh ether and decanted. The entrained solvent was removed to give 5.73 g of colorless material, melting point 120°–125° C. (s. 100°). Part of this material (2.31 g) was purified by dissolving in 100 ml of ethyl acetate and extracting with 25 ml of water (four times). The ethyl acetate was concentrated on a rotary evaporator, the residue (waxy solid) was dissolved in 20 ml of methanol and treated with 0.7 ml of 5.1N hydrogen chloride in ethanol. After evaporation of the solvent, the colorless HA367c foam-like material was triturated with 50 ml of ether and allowed to stand in the cold room overnight. The ether was decanted and the solid triturated with 25 ml of ether and decanted to give 2.13 g of product, melting point 90°–95° C. (foaming); $[\alpha]_D +62.5°$ (1% in methanol); $R_f$ 0.76 (18:1:1 dichloromethane-methanol-acetic acid).

Analysis Calc'd. for $C_{34}H_{33}F_3N_2O_3 \cdot HCl \cdot 0.5H_2O$: C, 65.85; H, 5.69; N, 4.51 Found: C, 65.88; H, 5.99; N, 4.42

EXAMPLE 46

(d-cis)-1-(2-Aminoethyl)-1,3,4,5-tetrahydro-3-hydroxy-4-(4-methoxyphenyl)-6-trifluoromethyl-2H-1-benzazepin-2-one A solution of 1.89 g (0.003 mol) of (d-cis)-1-(2-dibenzylaminoethyl)-1,3,4,5-tetrahydro-3-hydroxy-4-(4-methoxyphenyl)-6-trifluoromethyl-2H-1-benzazepin-2-one, hydrochloride (see Example 45) in 100 ml of acetic acid was treated with a suspension of 2.0 g of 10% palladium on charcoal catalyst and placed under 50 psi of hydrogen on the Parr apparatus for six hours at room temperature. The catalyst was filtered, washed with acetic acid, and the filtrate concentrated on a rotary evaporator to give 2.06 g of an oily residue. This was dissolved in 100 ml of ethanol and treated with a suspension of 2.0 g of 10% palladium on charcoal in 25 ml of ethanol and placed on the Parr hydrogenator at 50 psi of hydrogen for six hours. The mixture was filtered through a bed of Celite and washed with ethanol. Evaporation of the filtrate gave a semi-solid residue which became granular after addition of 50 ml of ether. After cooling overnight, the solid was filtered and washed with ether; weight 0.76 g; melting point 95°–100° C. (foaming); $R_f$ 0.23 (8:1:1 dichloromethane-methanol-acetic acid).

Because this material was solvated and gave a high chlorine value, it was converted to the free base. A suspension of 0.71 g of material in 10 ml of water was treated portionwise with a solution of 0.20 g of potassium bicarbonate in 2 ml of water and extracted with 50 ml of ethyl acetate and 2 ml of methanol (to speed up separation of layers). The layers were separated and the aqueous phase was extracted with 50 ml of ethyl acetate (twice). The organic phases were combined, washed with 7 ml of water (twice), dried (magnesium sulfate), filtered and the solvent evaporated to give 0.55 g of colorless amorphous solid with an indefinite melting point (sintering at 60° C.); $R_f$ 0.23 (8:1:1 dichloromethane-methanol-acetic acid).

Analysis Calc'd. for $C_{20}H_{21}F_3N_2O_3.H_2O$: C, 59.54; H, 5.50; N, 6.95; F, 14.13 Found: C, 59.82; H, 5.56; N, 6.68; F, 14.16

Additional compounds falling within the scope of this invention are:

(cis)-3-(acetyloxy)-6-(t-butoxycarbonyl)-1-[2-(dimethylamino)ethyl]-1,3,4,5-tetrahydro-4-(4-methoxyphenyl)-2H-1-benzazepin-2-one (cis)-3-(acetyloxy)-6-(methylthio)-1-[2-(dimethylamino)ethyl]-1,3,4,5-tetrahydro-4-(4-methoxyphenyl)-2H-1-benzazepin-2-one (cis)-3-(acetyloxy)-6-(methoxy)-1-2-(dimethylamino)ethyl]-1,3,4,5-tetrahydro-4-(4-methoxyphenyl)-2H-1-benzazepin-2-one (cis)-3-(acetyloxy)-7-[(N,N-dimethylamino)-carbonyl]-1-[2-(dimethylamino)ethyl]-1,3,4,5-tetrahydro-4-(4-methoxyphenyl)-2H-1-benzazepin-2-one (cis)-3-(acetyloxy)-7-(t-butoxycarbonyl)-1-[2-(dimethylamino)ethyl]-1,3,4,5-tetrahydro-4-(4-methoxyphenyl)-2H-1-benzazepin-2-one (cis)-3-(acetyloxy)-7-chloro-1-[2-(dimethylamino)ethyl]-1,3,4,5-tetrahydro-4-[4-(methylthio) phenyl]-2H-1-benzazepin-2-one

What is claimed is:

1. A compound having the formula

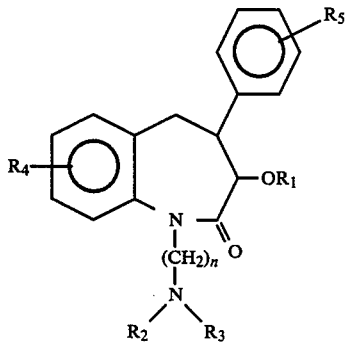

or a pharmaceutically acceptable salt thereof wherein
$R_1$ is hydrogen, alkyl, alkanoyl, alkenyl, arylcarbonyl, heteroarylcarbonyl or

$R_2$ and $R_3$ are each independently hydrogen, alkyl, cycloalkyl or arylalkyl or $R_2$ and $R_3$ together with the nitrogen atom to which they are attached are pyrrolidinyl, piperidinyl, or morpholinyl;
$R_4$ and $R_5$ are each independently hydrogen, halogen, alkyl, alkoxy, aryloxy, arylalkoxy, diarylalkoxy, arylalkyl, cyano, hydroxy, alkanoyloxy,

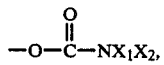

fluoro substituted alkoxy, fluoro substituted alkyl, (cycloalkyl)alkoxy, $-NO_2$, $-NX_3X_4$, $-S(O)_m$alkyl, $-S(O)_m$aryl,

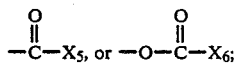

n is 2 or 3;
m is 0, 1 or 2;
$X_1$ and $X_2$ are each independently hydrogen, alkyl, aryl or heteroaryl, or $X_1$ and $X_2$ together with the nitrogen atom to which they are attached are pyrrolidinyl, piperidinyl or morpholinyl;
$X_3$ and $X_4$ are each independently hydrogen, alkyl, alkanoyl, arylcarbonyl, heteroacrylcarbonyl, or

$X_5$ is hydroxy, alkoxy, aryloxy, amino, alkylamino or dialkylamino; and
$X_6$ is alkyl, alkoxy or aryloxy; with the proviso that if $R_4$ is a 7-alkyl group, it must have a tertiary carbon atom bonded to the ring;
wherein the term "aryl" refers to phenyl and phenyl substituted with 1, 2 or 3 amino, alkylamino, dialkylamino, nitro, halogen, hydroxyl, trifluoromethyl, alkyl or 1 to 4 carbon atoms, alkoxy of 1 to 4 carbon atoms, alkanoyloxy, carbamoyl, or carboxyl groups;
the term "heteroaryl" refers to pyridinyl, pyrrolyl, imidazolyl, furyl, thienyl, or thiazolyl;
the terms "alkyl" and "alkoxy" refers to groups having 1 to 10 carbon atoms;
the term "alkenyl" refers to groups having 2 to 10 carbon atoms;
the term "alkanoyl" refers to groups having 2 to 11 carbon atoms; and
the term "cycloalkyl" refers to groups having 3, 4, 5, 6 or 7 carbon atoms.

2. A compound in accordance with claim 1 wherein $R_4$ and $R_5$ are each independently hydrogen, halogen, alkyl, alkoxy, aryloxy, arylalkoxy, arylalkyl, hydroxy, alkanoyloxy,

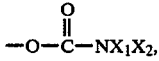

difluoromethoxy, trifluoromethyl, $-NX_3X_4$, 13 $S(O)_m$alkyl or $-S(O)_m$aryl;
$X_1$ and $X_2$ are each independently alkyl or heteroaryl; and
$X_3$ and $X_4$ are each independently alkyl, alkanoyl, arylcarbonyl, heteroarylcarbonyl, or

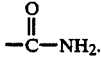

3. A compound in accordance with claim 1 wherein $R_2$ and $R_3$ are each independently alkyl or cycloalkyl.

4. A compound in accordance with claim 1 wherein $R_1$ is hydrogen.

5. A compound in accordance with claim 1 wherein $R_1$ is alkyl.

6. A compound in accordance with claim 1 wherein $R_1$ is alkanoyl, alkenyl, arylcarbonyl, heteroarylcarbonyl or

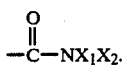

7. A compound in accordance with claim 6 wherein R₁ is alkanoyl.

8. A compound in accordance with claim 7 wherein R₁ is acetyl.

9. A compound in accordance with claim 1 wherein R₂ and R₃ are each alkyl.

10. A compound in accordance with claim 9 wherein R₂ and R₃ are each methyl.

11. A compound in accordance with claim 1 wherein R₂ and R₃ are each cycloalkyl.

12. A compound in accordance with claim 1 wherein R₂ and R₃ together with the nitrogen atom to which they are attached are pyrrolidinyl, piperidinyl or morpholinyl.

13. A compound in accordance with claim 1 wherein R₄ is hydrogen.

14. A compound in accordance with claim 1 wherein R₄ is halogen.

15. A compound in accordance with claim 1 wherein R₄ is chlorine and is located in the 7-position of the benzazepine nucleus.

16. A compound in accordance with claim 1 wherein R₄ is trifluoromethyl and is located in the 6-position of the benzazepine nucleus.

17. A compound in accordance with claim 1 wherein R₄ is trifluoromethyl and is located in the 7-position of the benzazepine nucleus.

18. A compound in accordance with claim 1 wherein R₅ is alkoxy.

19. A compound in accordance with claim 1 wherein R₅ is methoxy and is located in the 4-position of the phenyl ring to which it is attached.

20. A compound in accordance with claim 1 wherein n is 2.

21. A compound in accordance with claim 1 wherein n is 3.

22. The d-cis enantiomer of a compound of claim 1.

23. A compound in accordance with claim 1 wherein R₁ is alkanoyl, R₂ and R₃ are each alkyl, R₄ is 6- or 7-trifluoromethyl, R₅ is alkoxy and is located in the 4-position of the ring to which it is attached, and n is 2.

24. The compound in accordance with claim 1, (cis)-3-(acetyloxy)-7-chloro-1-[2-(dimethylamino)ethyl]-1,3,4,5-tetrahydro-4-(4-methoxyphenyl)-2H 1-benzazepin-2-one or a pharmaceutically acceptable salt thereof.

25. The compound in accordance with claim 1, (cis)-3-(acetyloxy)-1-[2-(dimethylamino)ethyl]-1,3,4,5-tetrahydro-4-(4-methoxyphenyl)-2H-1-benzazepin-2-one or a pharmaceutically acceptable salt thereof.

26. The compound in accordance with claim 1, (trans)-3-(acetyloxy)-1-2-(dimethylamino)ethyl]-1,3,4,5-tetrahydro-4-(4-methoxyphenyl)-2H-1-benzazepin-2-one, or a pharmaceutically acceptable salt thereof.

27. The compound in accordance with claim 1, (cis)-3-(acetyloxy)-1-[2-(dimethylamino)ethyl]-1,3,4,5-tetrahydro-4-(4-methoxyphenyl)-7-(trifluoromethyl)-2H-1-benzazepin-2-one, or a pharmaceutically acceptable salt thereof.

28. The compound in accordance with claim 1, (cis)-3-(acetyloxy)-7-(methoxy)-1-2-(dimethylamino)ethyl]-1,3,4,5-tetrahydro-4-(4-methoxyphenyl)-2H 2-one, or a pharmaceutically acceptable salt thereof.

29. The compound in accordance with claim 1, (d-cis)-3-(acetyloxy)-1-[2-(dimethylamino)ethyl]-1,3,4,5-tetrahydro-4-(4-methoxyphenyl)-6-(trifluoro-methyl)-2H-1-benzazepin-2-one, or a pharmaceutically acceptable salt thereof.

30. The compound in accordance with claim 1, (d-cis)-3-(acetyloxy)-1,3,4,5-tetrahydro-4-(4-methoxyphenyl)-1-[2-(methylamino)ethyl]-6-(trifluoromethyl)-2H-1-benzazepin-2-one, or a pharmaceutically acceptable salt thereof.

* * * * *